(12) United States Patent
Takiguchi et al.

(10) Patent No.: US 7,597,955 B2
(45) Date of Patent: Oct. 6, 2009

(54) LIGHT-EMITTING DEVICE, ORGANIC COMPOUND AND DISPLAY

(75) Inventors: Takao Takiguchi, Tokyo (JP); Shinjiro Okada, Kamakura (JP); Akira Tsuboyama, Tokyo (JP); Satoshi Igawa, Fujisawa (JP); Jun Kamatani, Tokyo (JP); Masashi Hashimoto, Kawasaki (JP); Minako Nakasu, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 465 days.

(21) Appl. No.: 10/573,789

(22) PCT Filed: Nov. 19, 2004

(86) PCT No.: PCT/JP2004/017643
§ 371 (c)(1),
(2), (4) Date: Mar. 28, 2006

(87) PCT Pub. No.: WO2005/051046
PCT Pub. Date: Jun. 2, 2005

(65) Prior Publication Data
US 2007/0057250 A1    Mar. 15, 2007

(30) Foreign Application Priority Data
Nov. 21, 2003   (JP) ............................. 2003-392090
Nov. 10, 2004   (JP) ............................. 2004-325838

(51) Int. Cl.
*B32B 5/16*   (2006.01)
*G01N 21/01*   (2006.01)

(52) U.S. Cl. ................ 428/327; 428/328; 356/244
(58) Field of Classification Search ................ 428/327, 428/328, 331; 356/244; 209/587
See application file for complete search history.

(56) References Cited

U.S. PATENT DOCUMENTS 5,726,750 A * 3/1998 Ito et al. ................ 356/244
6,803,097 B2 * 10/2004 Roitman et al. ............ 428/327

FOREIGN PATENT DOCUMENTS

| JP | 2002-43056 | 2/2002 |
|---|---|---|
| JP | 2002-359079 | 12/2002 |
| JP | 2003-268362 | 9/2003 |
| JP | 2004-14155 | 1/2004 |
| WO | WO 03/080760 | 10/2003 |

* cited by examiner

Primary Examiner—Marcos D. Pizarro
Assistant Examiner—Steven H Rao
(74) Attorney, Agent, or Firm—Fitzpatrick, Cella, Harper & Scinto

(57) ABSTRACT

There are provided an organic light-emitting device having a light output of a high emission efficiency and a high luminance and having high durability and a novel organic compound that enables the device to be attained. An organic compound of a long fluorescence lifetime represented by an organic compound having, in a molecule, at least one partial structure comprising an unsubstituted or substituted indole ring and at least one partial structure comprising an unsubstituted or substituted carbazole ring is used in an organic light-emitting device.

9 Claims, 4 Drawing Sheets

LIGHT-EMITTING DEVICE, ORGANIC COMPOUND AND DISPLAY

CROSS-REFERENCE TO RELATED APPLICATIONS

This application is a submission to enter the national phase stage under 35 U.S.C. §371 of PCT Application No. PCT/JP2004/017643, filed Nov. 19, 2004.

TECHNICAL FIELD

The present invention relates to a novel organic compound for a light-emitting device and an organic light-emitting device (also referred to as organic electroluminescence device or organic EL device) used for a surface light source, a flat panel display, etc.

BACKGROUND ART

As for organic light-emitting device, there was an example in the past to cause light emission by applying a voltage on an anthracene vapor-deposited film (Thin Solid Films, 94 (1982) 171) and the like. In recent years, however, in view of the advantages that a large area product can be obtained more easily as compared with an inorganic light-emitting device, desired color can be attained by development of various new materials and that it can be operated at low voltage and expected as a light-emitting device with a high-speed response and a high emission efficiency, application researches for device implementation as well as materials development are vigorously conducted.

For example, as described in detail in Macromol. Symp. 125, 1-48 (1997), an organic EL device has generally a structure comprising two layers of upper and lower electrodes formed on a transparent substrate and an organic layer comprising a light-emitting layer formed therebetween.

Recently, in addition to conventional devices utilizing fluorescence on transition from excited singlet state to ground state, devices utilizing phosphorescence via triplet exciton have been studied as represented by the following references: "Improved energy transfer in electrophosphorescent device" (D. F. O'Brien et al., Applied Physics Letters Vol. 74, No. 3, p. 422 (1999)) and "Very high-efficiency green organic light-emitting devices based on electrophosphorescence" (M. A. Baldo et al., Applied Physics Letters Vol. 75, No. 1, p. 4 (1999)). In these references, organic layers of four-layer structure are mainly used. They are composed of a hole-transporting layer, a light-emitting layer, an exciton diffusion-prevention layer and an electron-transporting layer from the side of an anode. The materials used are a carrier-transporting material and a phosphorescent material Ir(ppy)$_3$.

Further, by using various types of fluorescent organic compounds, emission of a light of ultraviolet to infrared region, and, recently, researches on various compounds are actively conducted.

Moreover, other than the above-mentioned organic light-emitting devices using low molecule materials, an organic light-emitting device using a conjugated polymer was reported by a group of Cambridge University (Nature, 347, 539 (1990)). According to this report, a film of polyphenylenevinylene (PPV) was formed using a coating system and light emission from a single layer was confirmed.

As described above, the latest progress of organic light-emitting devices is remarkable, and their characteristic possibility of attaining a thin, lightweight, light-emitting device with a high luminance at a low applied voltage, a variety of emission wavelengths, and a high-speed response suggests their applicability to various uses.

However, at present, a light output of a higher luminance or a higher conversion efficiency is still required. Moreover, there are still many problems in respect of durability such as time-dependent change during prolonged use and degradation by an atmospheric gas including oxygen, moisture and the like. Furthermore, although in consideration of application to full-color display or the like, light emission of blue, green and red with a high color purity is needed, this problem has not been sufficiently resolved.

Moreover, although a number of aromatic compounds and condensed polycyclic aromatic compounds have been studied as a fluorescent organic compound for use in an electron-transporting layer and a light-emitting layer, etc., it is hard to say that those having sufficiently satisfying emission luminance and durability have been obtained.

Further, Japanese Patent No. 3,229,654 and Japanese Patent Application Laid-Open No. 2002-305084 can be mentioned as patent references to indole compounds related to those used in the present invention. However, they do not disclose those organic compound in accordance with the present invention characterized by having both a partial structure containing an indole ring and a partial structure containing a carbazole ring in a molecule structure.

DISCLOSURE OF THE INVENTION

It is, therefore, an object of the present invention to provide an organic light-emitting device having a light output of a high emission efficiency and a high luminance and having high durability.

It is another object of the present invention to provide a novel organic compound that enables the above object to be attained.

It is still another object of the present invention to provide an organic light-emitting device that can be easily produced at a relatively low cost.

These objects are attained by the following means.

1. A compound having a fluorescence lifetime of 880 ms or more at 77K represented by a novel organic compound in accordance with the present invention is used in an organic light-emitting device.

2. A light-emitting layer in which the fluorescence lifetime at 77K of a host material is $5.8 \times 10^5$ or more times the fluorescence lifetime of a light-emitting material is used in an organic light-emitting device.

3. A novel organic compound of the present invention characterized by having, in a molecule, at least one partial structure comprising an unsubstituted or substituted indole ring and at least one partial structure comprising an unsubstituted or substituted carbazole ring is used in an organic light-emitting device.

BEST MODE FOR CARRYING OUT THE INVENTION

Figure 1A:
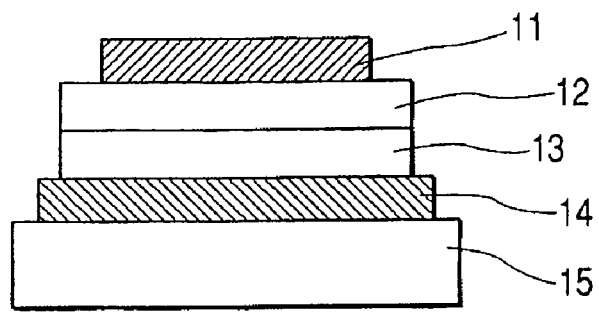
FIGS. 1A, 1B and 1C are schematic views showing examples of the light-emitting device of the present invention.

Using the organic compound having a long fluorescence lifetime at 77K represented by the novel compound in accordance with the present invention enables the above objects to be attained, and an organic compound having a fluorescence lifetime of 880 ms or more at 77K, more preferably 1100 ms or more is suitable.

Further, it is preferable that the organic compound having a long fluorescence lifetime at 77K is used in a light-emitting layer and more preferable that the organic compound is used as a host material in a light-emitting layer comprised of at least one host material and at lest one light-emitting material.

Moreover, it is preferable that the fluorescence lifetime at 77K of the host material of the light-emitting layer is $5.8 \times 10^5$ or more times the fluorescence lifetime of the light-emitting material of the light-emitting layer.

Further, it is preferable that the light-emitting material of the light-emitting layer is a metal coordination compound, and more preferable that the metal coordination compound is an iridium coordination compound.

Moreover, the partial structure comprising an unsubstituted or substituted indole ring of the novel organic compound of the present invention includes a structure represented by the following general formula (1), and the partial structure comprising an unsubstituted or substituted carbazole ring includes a structure represented by the following general formula (2):

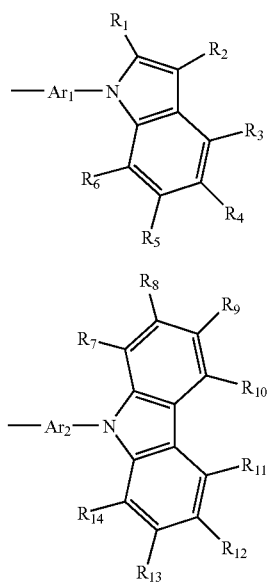

In the general formulae (1) and (2), $A_1$ and $A_2$ independently represents a single bond, an unsubstituted or substituted arylene group, or an unsubstituted or substituted divalent heterocyclic group and preferably include a single bond, phenylene, biphenylene, terphenylene, naphthylene, fluorenediyl, anthracenediyl, thiophenediyl, pyridinediyl, quinolinediyl, and phenanthrenediyl with phenylene, biphenylene, naphthylene, fluorenediyl, pyridinediyl, and quinolinediyl being more preferable.

Further, $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ is independently selected from an hydrogen atom, a halogen atom, a linear or branched alkyl group having 1-20 carbon atoms (wherein one methylene group or two or more non-adjacent methylene groups of the alkyl group may be replaced by —O—, —S—, —CO—, —CO—O—, —O—CO—, —CH=CH—, or —C≡C—, or one or more methylene groups may be replaced by an unsubstituted or substituted arylene group or an unsubstituted or substituted divalent heterocyclic group, and a hydrogen atom in the alkyl group may be replaced by a fluorine atom), an unsubstituted or substituted aryl group, and an unsubstituted or substituted heterocyclic group. They are preferably a hydrogen atom, a halogen atom, a linear alkyl group having 1-10 carbon atoms (wherein one methylene group or two or more non-adjacent methylene groups of the alkyl group may be replaced by —O— and a hydrogen atom in the alkyl group may be replaced by a fluorine atom), an unsubstituted or substituted phenyl group, or naphthyl group with a hydrogen atom, a fluorine atom, a bromine atom, a linear alkyl group having 1-5 carbon atoms (wherein one methylene group in the alkyl group may be replaced by —O—, and a hydrogen atom in the alkyl group may be replaced by a fluorine atom) and an unsubstituted or substituted phenyl group being more preferable.

Moreover, adjacent ones of $R_3$, $R_4$, $R_5$, $R_6$, $R_7$, $R_8$, $R_9$, $R_{10}$, $R_{11}$, $R_{12}$, $R_{13}$, and $R_{14}$ can be bonded together to form a ring structure.

Specific examples of the organic compound having the partial structures represented by the general formulae (1) and (2) include a structure represented by the following general formula (3):

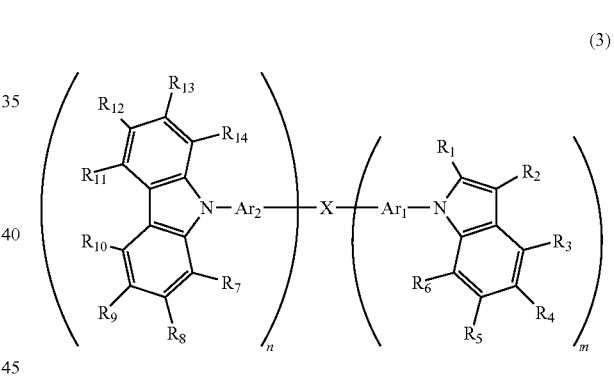

In the general formula (3), m and n are independently an integer of 1-5, preferably an integer of 1-3, and the sum of m and n is an integer of 2-6, preferably an integer of integer of 2-4.

Further, X is an unsubstituted or substituted m+n valent organic group, preferably a m+n valent group having a benzene, pyridine, pyridazine, pyrazine, triazine, or tetrazine structure, and more preferably a m+n valent group having a benzene, pyridine, pyrazine, or triazine structure.

Of the compounds represented by the general formula (3), compounds represented by the following general formula (4) are preferable, and compounds represented by the following general formula (5) are more preferable.

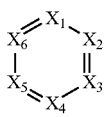

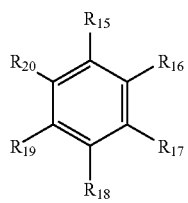

(5)

In the general formula (4) $X_1$ represents a nitrogen atom or C—$R_{15}$, $X_2$ represents a nitrogen atom or C—$R_{16}$, $X_3$ represents a nitrogen atom or C—$R_{17}$, $X_4$ represents a nitrogen atom or C—$R_{18}$, $X_5$ represents a nitrogen atom or C—$R_{19}$, $X_6$ represents a nitrogen atom or C—$R_{20}$, and the number of nitrogen atoms in $X_1$ to $X_6$ is 4 or less, preferably 3 or less.

In the general formulae (4) and (5), $R_{15}$, $R_{16}$, $R_{17}$, $R_{18}$, $R_{19}$, and $R_{20}$ is independently selected from an hydrogen atom, a halogen atom, a linear or branched alkyl group having 1-20 carbon atoms (wherein one methylene group or two or more non-adjacent methylene groups of the alkyl group may be replaced by —O—, —S—, —CO—, —CO—O—, —O—CO—, —CH=CH—, or —C≡C—, or one or more methylene groups may be replaced by an unsubstituted or substituted arylene group or an unsubstituted or substituted divalent heterocyclic group, and a hydrogen atom in the alkyl group may be replaced by a fluorine atom), an unsubstituted or substituted aryl group, and an unsubstituted or substituted heterocyclic group. They are preferably a hydrogen atom, a halogen atom, a linear alkyl group having 1-10 carbon atoms (wherein one methylene group or two or more non-adjacent methylene groups of the alkyl may be replaced by —O—, and a hydrogen atom in the alkyl group may be replaced by a fluorine atom), an unsubstituted or substituted phenyl group, or naphthyl group, more preferably a hydrogen atom, a fluorine atom, a bromine atom, and a linear alkyl group having 1-5 carbon atoms (wherein one methylene group of the alkyl group may be replaced by —O—, and a hydrogen atom in the alkyl group may be replaced by a fluorine atom), and an unsubstituted or substituted phenyl group.

However, in the general formulae (4) and (5), at least one of $R_{15}$ to $R_{20}$ is a partial structure comprising an indole ring represented by the general formula (1) and at least one is a partial structure comprising a carbazole ring represented by the general formula (2), and it is preferable that at least three of $R_{15}$ to $R_{20}$ are each a partial structure comprising an indole ring represented by the general formula (1) or a partial structure comprising a carbazole ring represented by the general formula (2).

Specific structural formulae of the organic compounds represented by the general formula (3) are shown in Tables 1 to 20 below. However, these are only representative examples for the purpose of illustration and the present invention is not limited thereto.

Incidentally, the abbreviations used in the column of X in Tables 1 to 20 represent the following structures. A colon ":" following the abbreviation has the meaning "represents".

Ph2A:

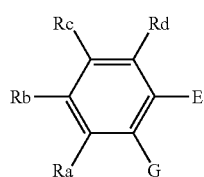

Ph2B:

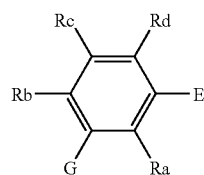

Ph2C:

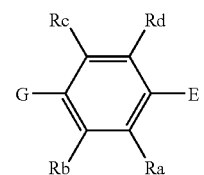

Ph3A:

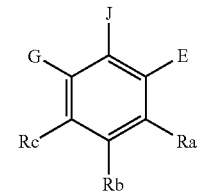

Ph3B:

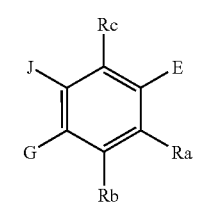

Ph3C:

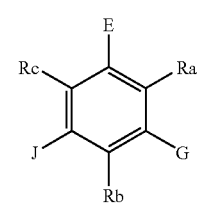

Ph4A:

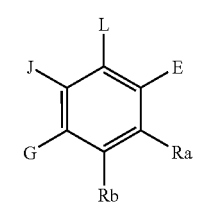

Ph4B:

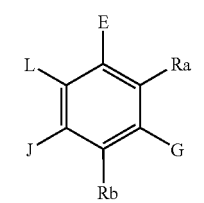

Ph4C:
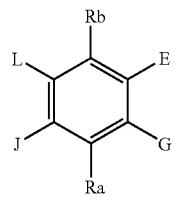
Ph5:
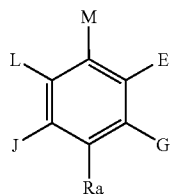
Ph6:
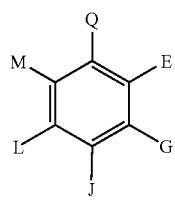
Pi2A:
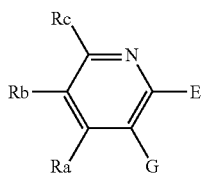
Pd2A:
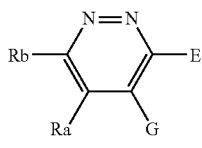
Pz2A:
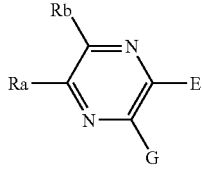
Pi2B:
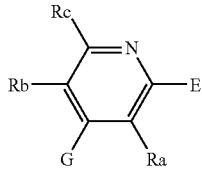
Pi2C:
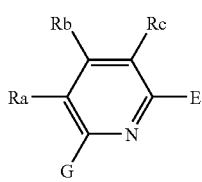
Pz2B:
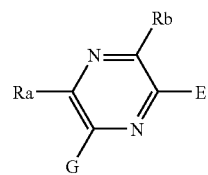
Tr2A:
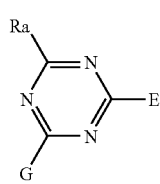
Pi2D:
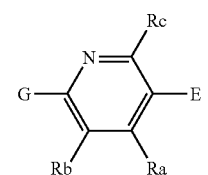
Pd2B:
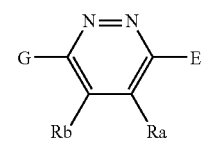
Pz2C:
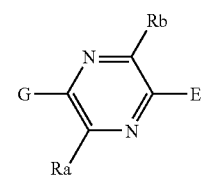
Pm2A:
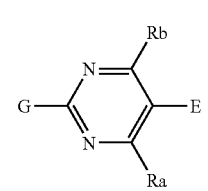
Tr2B:
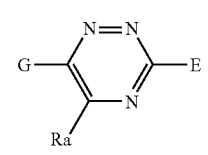
Te2A:
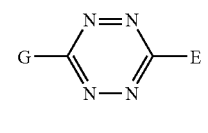
Pi3A:
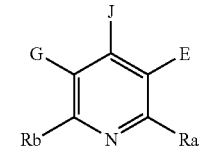

Pd3A: 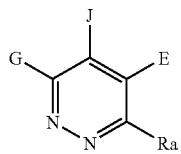
Pi3B: 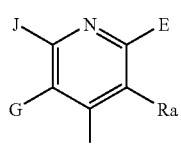
Pz3B: 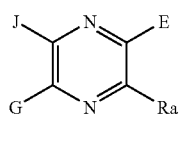
Pi3C: 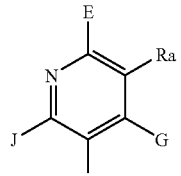
Tr3A: 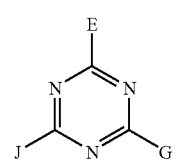
Pd4A: 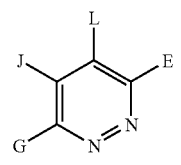
Pi4A: 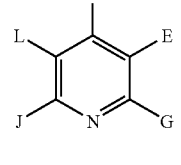
Pz4A: 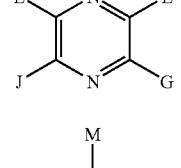
Pi5A: 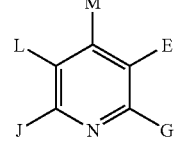
N: 
The abbreviations used in the columns of $A_1$ and $A_2$ represent the following structures.
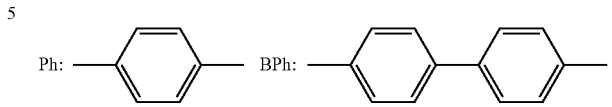
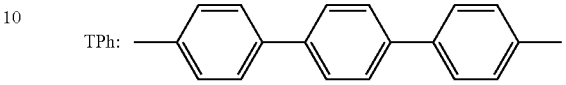
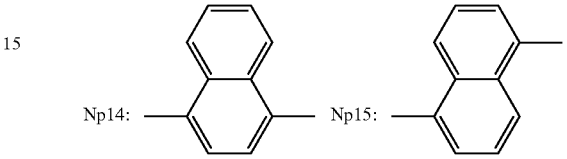
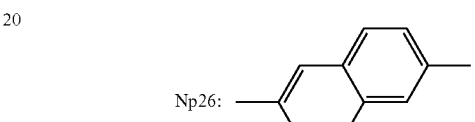
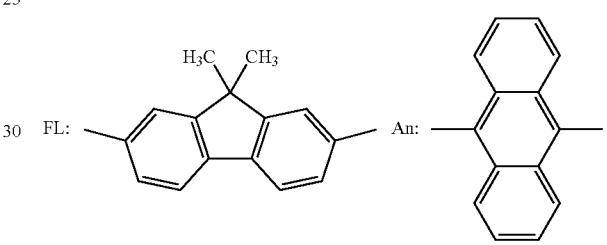
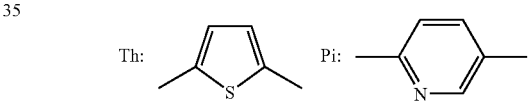
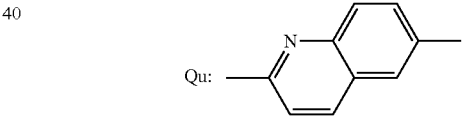
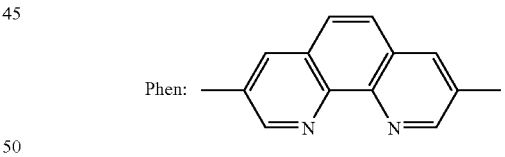
The abbreviations used in the columns of $R_a$ to $R_d$ and $R_1$ to $R_{15}$ represent the following structures. CH3: $CH_3$ OCH3: $OCH_3$ CF3: $CF_3$ C2H5: $C_2H_5$ C3H7: $C_3H_7$ OCF3: $OCF_3$ OC2H5: $OC_2H_5$ C(CH3)3: $C(CH_3)_3$ OCH2C3F7: $OCH_2C_3F_7$
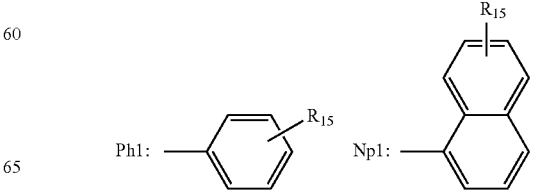

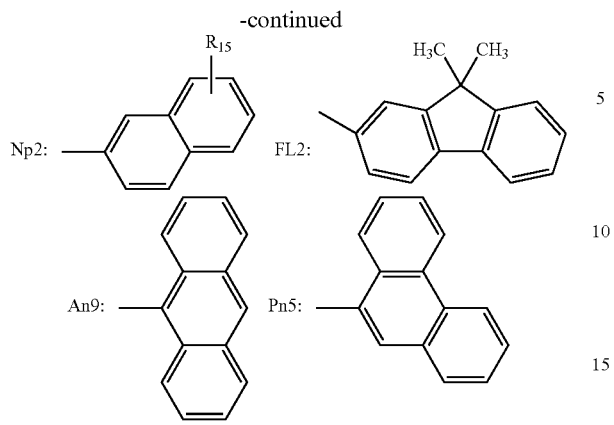
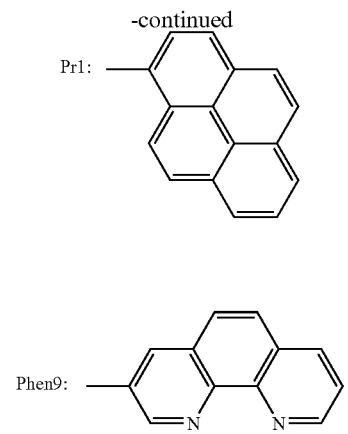

TABLE 1

| No. | X | E | G | Ra | Rb | Rc | Rd | m | n | A₁ | R₁ | R₂ | R₃ | R₄ |
|---|---|---|---|---|---|---|---|---|---|---|---|---|---|---|
| 1 | Ph2A | (1) | (2) | H | H | H | H | 1 | 1 | — | H | H | H | H |
| 2 | Ph2A | (1) | (2) | H | H | H | H | 1 | 1 | Ph | CH3 | Ph1 | H | H |
| 3 | Ph2A | (1) | (2) | H | H | H | H | 1 | 1 | — | H | CH3 | H | Ph1 |
| 4 | Ph2A | (1) | (2) | CH3 | H | H | H | 1 | 1 | Ph | CH3 | CH3 | H | H |
| 5 | Ph2A | (1) | (2) | H | H | H | H | 1 | 1 | Ph | Ph1 | H | H | H |
| 6 | Ph2A | (1) | (2) | H | H | H | H | 1 | 1 | Ph | H | Ph1 | H | H |
| 7 | Ph2A | (1) | (2) | H | H | Br | H | 1 | 1 | Ph | Ph1 | Ph1 | H | H |
| 8 | Ph2A | (1) | (2) | H | H | H | H | 1 | 1 | BPh | H | Ph1 | H | H |
| 9 | Ph2A | (1) | (2) | H | H | H | H | 1 | 1 | Ph | Ph1 | Ph1 | H | H |
| 10 | Ph2A | (1) | (2) | H | H | H | H | 1 | 1 | Np14 | Ph1 | H | H | H |
| 11 | Ph2B | (1) | (2) | H | H | H | H | 1 | 1 | — | Np2 | H | H | H |
| 12 | Ph2B | (1) | (2) | H | H | H | H | 1 | 1 | Ph | CH3 | H | H | H |
| 13 | Ph2B | (1) | (2) | H | H | H | H | 1 | 1 | — | H | C3H7 | H | H |
| 14 | Ph2B | (1) | (2) | H | H | H | H | 1 | 1 | Ph | CH3 | CH3 | H | H |
| 15 | Ph2B | (1) | (2) | H | H | H | H | 1 | 1 | Ph | Ph1 | H | H | H |
| 16 | Ph2B | (1) | (2) | H | H | H | H | 1 | 1 | TPh | H | Ph1 | H | H |
| 17 | Ph2B | (1) | (2) | H | F | H | H | 1 | 1 | Ph | Ph1 | Ph1 | H | H |
| 18 | Ph2B | (1) | (2) | H | H | H | H | 1 | 1 | Ph | H | Ph1 | H | H |
| 19 | Ph2B | (1) | (2) | H | H | H | H | 1 | 1 | Ph | Ph1 | Ph1 | H | H |
| 20 | Ph2B | (1) | (2) | H | H | H | H | 1 | 1 | FL | Ph1 | H | H | H |

| No. | R₅ | R₆ | A₂ | R₇ | R₈ | R₉ | R₁₀ | R₁₁ | R₁₂ | R₁₃ | R₁₄ | R₁₅ |
|---|---|---|---|---|---|---|---|---|---|---|---|---|
| 1 | H | H | — | H | H | H | H | H | H | H | H | H |
| 2 | H | H | — | H | H | H | H | H | H | H | H | OCH3 |
| 3 | H | H | Ph | H | H | H | H | H | H | H | H | CF3 |
| 4 | H | H | Ph | H | H | H | H | H | H | H | H | H |
| 5 | H | H | — | H | H | CH3 | H | H | H | H | H | H |
| 6 | H | H | — | H | H | H | H | H | H | H | H | F |
| 7 | H | H | — | H | H | H | H | H | H | H | H | H |
| 8 | H | H | Ph | H | H | H | H | H | H | H | H | H |
| 9 | H | H | Ph | H | H | H | H | H | H | H | H | H |
| 10 | H | H | — | H | H | H | H | H | H | H | H | H |
| 11 | H | H | — | H | H | H | H | H | H | H | H | H |
| 12 | H | H | — | H | H | C2H5 | H | H | H | H | H | H |
| 13 | H | H | Ph | H | H | H | H | H | H | H | H | H |
| 14 | H | H | Ph | H | H | H | H | H | H | H | H | H |
| 15 | H | H | — | H | H | H | H | H | H | H | H | H |
| 16 | H | H | — | H | H | H | H | H | H | H | H | H |
| 17 | H | H | — | H | H | H | H | H | H | H | H | H |
| 18 | H | H | Ph | H | H | H | H | H | H | H | H | H |
| 19 | H | H | Ph | H | H | H | H | H | H | H | H | H |
| 20 | H | H | — | H | H | H | H | H | H | H | H | H |

TABLE 2

| No. | X | E | G | Ra | Rb | Rc | Rd | m | n | A₁ | R₁ | R₂ | R₃ | R₄ | R₅ |
|---|---|---|---|---|---|---|---|---|---|---|---|---|---|---|---|
| 21 | Ph2C | (1) | (2) | H | H | H | H | 1 | 1 | — | H | H | H | H | H |
| 22 | Ph2C | (1) | (2) | H | H | H | H | 1 | 1 | Ph | H | H | H | H | H |

TABLE 2-continued

| No. | X | E | G | J | Ra | Rb | Rc | m | n | A₁ | R₁ | R₂ | R₃ | R₄ | R₅ |
|---|---|---|---|---|---|---|---|---|---|---|---|---|---|---|---|
| 23 | Ph2C | (1) | (2) | H | H | H | H | 1 | 1 | Ph | H | H | H | H | H |
| 24 | Ph2C | (1) | (2) | H | H | H | H | 1 | 1 | — | CH3 | H | H | H | H |
| 25 | Ph2C | (1) | (2) | H | H | H | H | 1 | 1 | Ph | CH3 | H | H | H | H |
| 26 | Ph2C | (1) | (2) | H | H | H | H | 1 | 1 | Ph | CH3 | H | H | H | H |
| 27 | Ph2C | (1) | (2) | H | H | H | H | 1 | 1 | — | H | CH3 | H | H | H |
| 28 | Ph2C | (1) | (2) | H | H | H | H | 1 | 1 | Ph | H | CH3 | H | H | H |
| 29 | Ph2C | (1) | (2) | H | H | H | H | 1 | 1 | Ph | H | CH3 | H | H | H |
| 30 | Ph2C | (1) | (2) | H | H | H | H | 1 | 1 | — | CH3 | CH3 | H | H | H |
| 31 | Ph2C | (1) | (2) | H | H | H | H | 1 | 1 | Ph | CH3 | CH3 | H | H | H |
| 32 | Ph2C | (1) | (2) | H | H | H | H | 1 | 1 | Ph | CH3 | CH3 | H | H | H |
| 33 | Ph2C | (1) | (2) | H | H | H | H | 1 | 1 | — | Ph1 | H | H | H | H |
| 34 | Ph2C | (1) | (2) | H | H | H | H | 1 | 1 | Ph | Ph1 | H | H | H | H |
| 35 | Ph2C | (1) | (2) | H | H | H | H | 1 | 1 | Ph | Ph1 | H | H | H | H |
| 36 | Ph2C | (1) | (2) | H | H | H | H | 1 | 1 | Ph | Ph1 | H | H | H | H |
| 37 | Ph2C | (1) | (2) | H | H | H | H | 1 | 1 | Ph | Ph1 | H | H | H | H |
| 38 | Ph2C | (1) | (2) | H | H | H | H | 1 | 1 | Ph | Ph1 | H | H | H | H |
| 39 | Ph2C | (1) | (2) | H | H | H | H | 1 | 1 | — | H | Ph1 | H | H | H |
| 40 | Ph2C | (1) | (2) | H | H | H | H | 1 | 1 | Ph | H | Ph1 | H | H | H |
| 41 | Ph2C | (1) | (2) | H | H | H | H | 1 | 1 | Ph | H | Ph1 | H | H | H |
| 42 | Ph2C | (1) | (2) | H | H | H | H | 1 | 1 | Ph | H | Ph1 | H | H | H |
| 43 | Ph2C | (1) | (2) | H | H | H | H | 1 | 1 | Ph | H | Ph1 | H | H | H |
| 44 | Ph2C | (1) | (2) | H | H | H | H | 1 | 1 | Ph | H | Ph1 | H | H | H |
| 45 | Ph2C | (1) | (2) | H | H | H | H | 1 | 1 | — | Ph1 | Ph1 | H | H | H |
| 46 | Ph2C | (1) | (2) | H | H | H | H | 1 | 1 | Ph | Ph1 | Ph1 | H | H | H |
| 47 | Ph2C | (1) | (2) | H | H | H | H | 1 | 1 | Ph | Ph1 | Ph1 | H | H | H |
| 48 | Ph2C | (1) | (2) | H | H | H | H | 1 | 1 | Ph | Ph1 | Ph1 | H | H | H |
| 49 | Ph2C | (1) | (2) | Ph | H | H | Ph | 1 | 1 | Ph | Ph1 | Ph1 | H | H | H |
| 50 | Ph2C | (1) | (2) | H | H | H | H | 1 | 1 | Np26 | Ph1 | Ph1 | H | H | H |

| No. | R₆ | A₂ | R₇ | R₈ | R₉ | R₁₀ | R₁₁ | R₁₂ | R₁₃ | R₁₄ | R₁₅ |
|---|---|---|---|---|---|---|---|---|---|---|---|
| 21 | H | — | H | H | H | H | H | H | H | H | H |
| 22 | H | — | H | H | H | H | H | H | H | H | H |
| 23 | H | Ph | H | H | H | H | H | H | H | H | H |
| 24 | H | — | H | H | H | H | H | H | H | H | H |
| 25 | H | — | H | H | H | H | H | H | H | H | H |
| 26 | H | Ph | H | H | H | H | H | H | H | H | H |
| 27 | H | — | H | H | H | H | H | H | H | H | H |
| 28 | H | — | H | H | H | H | H | H | H | H | H |
| 29 | H | Ph | H | H | H | H | H | H | H | H | H |
| 30 | H | — | H | H | H | H | H | H | H | H | H |
| 31 | H | — | H | H | H | H | H | H | H | H | H |
| 32 | H | Ph | H | H | H | H | H | H | H | H | H |
| 33 | H | — | H | H | H | H | H | H | H | H | H |
| 34 | H | — | H | H | H | H | H | H | H | H | H |
| 35 | H | Ph | H | H | H | H | H | H | H | H | H |
| 36 | H | — | H | H | H | H | H | H | H | H | CH3 |
| 37 | H | — | H | H | H | H | H | H | H | H | F |
| 38 | H | — | H | H | C2H5 | H | H | H | H | H | H |
| 39 | H | — | H | H | H | H | H | H | H | H | H |
| 40 | H | — | H | H | H | H | H | H | H | H | H |
| 41 | H | Ph | H | H | H | H | H | H | H | H | H |
| 42 | H | — | H | H | H | H | H | H | H | H | OCH3 |
| 43 | H | — | H | H | H | H | H | H | H | H | CF3 |
| 44 | H | — | H | H | H | H | H | H | H | H | Cl |
| 45 | H | — | H | H | H | H | H | H | H | H | H |
| 46 | H | — | H | H | H | H | H | H | H | H | H |
| 47 | H | Ph | H | H | H | H | H | H | H | H | H |
| 48 | H | — | H | H | CH3 | H | H | H | H | H | H |
| 49 | H | — | H | H | H | H | H | H | H | H | H |
| 50 | H | — | H | H | H | H | H | H | H | H | H |

TABLE 3

| No. | X | E | G | J | Ra | Rb | Rc | m | n | A₁ | R₁ | R₂ | R₃ | R₄ | R₅ |
|---|---|---|---|---|---|---|---|---|---|---|---|---|---|---|---|
| 51 | Ph3A | (1) | (1) | (2) | H | H | H | 2 | 1 | — | H | H | H | H | H |
| 52 | Ph3A | (1) | (1) | (2) | H | H | H | 2 | 1 | Ph | CH3 | Ph1 | H | H | H |
| 53 | Ph3A | (1) | (1) | (2) | H | H | H | 2 | 1 | — | Ph1 | CH3 | H | H | H |
| 54 | Ph3A | (1) | (2) | (1) | H | H | H | 2 | 1 | Ph | CH3 | CH3 | H | H | H |
| 55 | Ph3A | (1) | (2) | (1) | H | H | H | 2 | 1 | Ph | Ph1 | H | H | H | H |
| 56 | Ph3A | (1) | (2) | (1) | H | H | H | 2 | 1 | Ph | H | Ph1 | H | H | H |
| 57 | Ph3A | (2) | (2) | (1) | H | H | H | 1 | 2 | Ph | Ph1 | Ph1 | H | H | H |
| 58 | Ph3A | (2) | (2) | (1) | H | H | H | 1 | 2 | Ph | H | Ph1 | H | H | H |
| 59 | Ph3A | (2) | (1) | (2) | H | H | H | 1 | 2 | Ph | Ph1 | Ph1 | H | H | H |
| 60 | Ph3A | (2) | (1) | (2) | H | H | H | 1 | 2 | Np14 | Ph1 | H | H | H | H |

TABLE 3-continued

| No. | X | E | G | J | Ra | Rb | Rc | m | n | A₁ | R₁ | R₂ | R₃ | R₄ | R₅ |
|---|---|---|---|---|---|---|---|---|---|---|---|---|---|---|---|
| 61 | Ph3B | (1) | (1) | (2) | H | H | H | 2 | 1 | — | H | Np1 | H | H | H |
| 62 | Ph3B | (1) | (1) | (2) | H | H | H | 2 | 1 | Ph | CH3 | H | H | H | H |
| 63 | Ph3B | (1) | (1) | (2) | H | H | H | 2 | 1 | — | H | C3H7 | H | H | H |
| 64 | Ph3B | (1) | (1) | (2) | H | H | H | 2 | 1 | Ph | CH3 | CH3 | H | H | H |
| 65 | Ph3B | (1) | (2) | (1) | H | H | H | 2 | 1 | Ph | Ph1 | H | H | H | H |
| 66 | Ph3B | (1) | (2) | (1) | H | H | H | 2 | 1 | Np15 | H | Ph1 | H | H | H |
| 67 | Ph3B | (2) | (2) | (1) | H | H | H | 1 | 2 | Ph | Ph1 | Ph1 | H | H | H |
| 68 | Ph3B | (2) | (2) | (1) | H | H | H | 1 | 2 | Ph | Ph1 | H | H | H | H |
| 69 | Ph3B | (2) | (1) | (2) | H | H | H | 1 | 2 | Ph | Ph1 | Ph1 | H | H | H |
| 70 | Ph3B | (2) | (1) | (2) | H | H | H | 1 | 2 | FL | Ph1 | H | H | H | H |

| No. | R₆ | A₂ | R₇ | R₈ | R₉ | R₁₀ | R₁₁ | R₁₂ | R₁₃ | R₁₄ | R₁₅ |
|---|---|---|---|---|---|---|---|---|---|---|---|
| 51 | H | An | H | H | H | H | H | H | H | H | H |
| 52 | H | — | H | H | H | H | H | H | H | H | OCH3 |
| 53 | H | Ph | H | H | H | H | H | H | H | H | CF3 |
| 54 | H | Ph | H | H | H | H | H | H | H | H | H |
| 55 | H | — | H | H | CH3 | H | H | H | H | H | H |
| 56 | H | Th | H | H | H | H | H | H | H | H | F |
| 57 | H | — | H | H | H | H | H | H | H | H | H |
| 58 | H | Ph | H | H | H | H | H | H | H | H | H |
| 59 | H | Ph | H | H | H | H | H | H | H | H | H |
| 60 | H | H | H | H | H | H | H | H | H | H | H |
| 61 | H | — | H | H | H | H | H | H | H | H | H |
| 62 | H | — | H | H | C2H5 | H | H | H | H | H | H |
| 63 | H | Ph | H | H | H | H | H | H | H | H | H |
| 64 | H | Ph | H | H | H | H | H | H | H | H | H |
| 65 | H | — | H | H | H | H | H | H | H | H | H |
| 66 | H | — | H | H | H | H | H | H | H | H | OCF3 |
| 67 | H | — | H | H | H | H | H | H | H | H | H |
| 68 | H | Ph | H | H | H | H | H | H | H | H | H |
| 69 | H | Ph | H | H | H | H | H | H | H | H | H |
| 70 | H | — | H | H | H | H | H | H | H | H | H |

TABLE 4

| No. | X | E | G | J | Ra | Rb | Rc | m | n | A₁ | R₁ | R₂ | R₃ | R₄ | R₅ |
|---|---|---|---|---|---|---|---|---|---|---|---|---|---|---|---|
| 71 | Ph3C | (1) | (1) | (2) | H | H | H | 2 | 1 | — | H | H | H | H | H |
| 72 | Ph3C | (1) | (1) | (2) | H | H | H | 2 | 1 | Ph | H | H | H | H | H |
| 73 | Ph3C | (1) | (1) | (2) | H | H | H | 2 | 1 | Ph | H | H | H | H | H |
| 74 | Ph3C | (1) | (1) | (2) | H | H | H | 2 | 1 | — | CH3 | H | H | H | H |
| 75 | Ph3C | (1) | (1) | (2) | H | H | H | 2 | 1 | Ph | CH3 | H | H | H | H |
| 76 | Ph3C | (1) | (1) | (2) | H | H | H | 2 | 1 | Ph | CH3 | H | H | H | H |
| 77 | Ph3C | (1) | (1) | (2) | H | H | H | 2 | 1 | — | H | CH3 | H | H | H |
| 78 | Ph3C | (1) | (1) | (2) | H | H | H | 2 | 1 | Ph | H | CH3 | H | H | H |
| 79 | Ph3C | (1) | (1) | (2) | H | H | H | 2 | 1 | Ph | H | CH3 | H | H | H |
| 80 | Ph3C | (1) | (1) | (2) | H | H | H | 2 | 1 | — | CH3 | CH3 | H | H | H |
| 81 | Ph3C | (1) | (1) | (2) | H | H | H | 2 | 1 | Ph | CH3 | CH3 | H | H | H |
| 82 | Ph3C | (1) | (1) | (2) | H | H | H | 2 | 1 | Ph | CH3 | CH3 | H | H | H |
| 83 | Ph3C | (1) | (1) | (2) | H | H | H | 2 | 1 | — | Ph1 | H | H | H | H |
| 84 | Ph3C | (1) | (1) | (2) | H | H | H | 2 | 1 | Ph | Ph1 | H | H | H | H |
| 85 | Ph3C | (1) | (1) | (2) | H | H | H | 2 | 1 | Ph | Ph1 | H | H | H | H |
| 86 | Ph3C | (1) | (1) | (2) | H | H | H | 2 | 1 | Ph | Ph1 | H | H | H | H |
| 87 | Ph3C | (1) | (1) | (2) | H | H | H | 2 | 1 | Ph | Ph1 | H | H | H | H |
| 88 | Ph3C | (1) | (1) | (2) | H | H | H | 2 | 1 | Ph | Ph1 | H | H | H | H |
| 89 | Ph3C | (1) | (1) | (2) | H | H | H | 2 | 1 | — | H | Ph1 | H | H | H |
| 90 | Ph3C | (1) | (1) | (2) | H | H | H | 2 | 1 | Ph | H | Ph1 | H | H | H |
| 91 | Ph3C | (1) | (1) | (2) | H | H | H | 2 | 1 | Ph | H | Ph1 | H | H | H |
| 92 | Ph3C | (1) | (1) | (2) | H | H | H | 2 | 1 | Ph | H | Ph1 | H | H | H |
| 93 | Ph3C | (1) | (1) | (2) | H | H | H | 2 | 1 | Ph | H | Ph1 | H | H | H |
| 94 | Ph3C | (1) | (1) | (2) | H | H | H | 2 | 1 | Ph | H | Ph1 | H | H | H |
| 95 | Ph3C | (1) | (1) | (2) | H | H | H | 2 | 1 | — | Ph1 | Ph1 | H | H | H |
| 96 | Ph3C | (1) | (1) | (2) | H | H | H | 2 | 1 | Ph | Ph1 | Ph1 | H | H | H |
| 97 | Ph3C | (1) | (1) | (2) | H | H | H | 2 | 1 | Ph | Ph1 | Ph1 | H | H | H |
| 98 | Ph3C | (1) | (1) | (2) | H | H | H | 2 | 1 | Ph | Ph1 | Ph1 | H | H | H |
| 99 | Ph3C | (1) | (1) | (2) | Ph | H | H | 2 | 1 | Ph | Ph1 | Ph1 | H | H | H |
| 100 | Ph3C | (1) | (1) | (2) | H | H | H | 2 | 1 | Np26 | Ph1 | Ph1 | H | H | H |

| No. | R₆ | A₂ | R₇ | R₈ | R₉ | R₁₀ | R₁₁ | R₁₂ | R₁₃ | R₁₄ | R₁₅ |
|---|---|---|---|---|---|---|---|---|---|---|---|
| 71 | H | — | H | H | H | H | H | H | H | H | H |
| 72 | H | — | H | H | H | H | H | H | H | H | H |
| 73 | H | Ph | H | H | H | H | H | H | H | H | H |
| 74 | H | — | H | H | H | H | H | H | H | H | H |
| 75 | H | — | H | H | H | H | H | H | H | H | H |

TABLE 4-continued

| No. | | | | | | | | | | | |
|---|---|---|---|---|---|---|---|---|---|---|---|
| 76 | H | Ph | H | H | H | H | H | H | H | H | H |
| 77 | H | — | H | H | H | H | H | H | H | H | H |
| 78 | H | — | H | H | H | H | H | H | H | H | H |
| 79 | H | Ph | H | H | H | H | H | H | H | H | H |
| 80 | H | — | H | H | H | H | H | H | H | H | H |
| 81 | H | — | H | H | H | H | H | H | H | H | H |
| 82 | H | Ph | H | H | H | H | H | H | H | H | H |
| 83 | H | — | H | H | H | H | H | H | H | H | H |
| 84 | H | — | H | H | H | H | H | H | H | H | H |
| 85 | H | Ph | H | H | H | H | H | H | H | H | H |
| 86 | H | — | H | H | H | H | H | H | H | H | $CH_3$ |
| 87 | H | — | H | H | H | H | H | H | H | H | F |
| 88 | H | — | H | H | $C_2H_5$ | H | H | H | H | H | H |
| 89 | H | — | H | H | H | H | H | H | H | H | H |
| 90 | H | — | H | H | H | H | H | H | H | H | H |
| 91 | H | Ph | H | H | H | H | H | H | H | H | H |
| 92 | H | — | H | H | H | H | H | H | H | H | $OCH_3$ |
| 93 | H | — | H | H | H | H | H | H | H | H | $CF_3$ |
| 94 | H | — | H | H | H | H | H | H | H | H | Cl |
| 95 | H | — | H | H | H | H | H | H | H | H | H |
| 96 | H | — | H | H | H | H | H | H | H | H | H |
| 97 | H | Ph | H | H | H | H | H | H | H | H | H |
| 98 | H | — | H | H | $CH_3$ | H | H | H | H | H | H |
| 99 | H | — | H | H | H | H | H | H | H | H | H |
| 100 | H | — | H | H | H | H | H | H | H | H | H |

TABLE 5

| No. | X | E | G | J | Ra | Rb | Rc | m | n | $A_1$ | $R_1$ | $R_2$ | $R_3$ | $R_4$ | $R_5$ |
|---|---|---|---|---|---|---|---|---|---|---|---|---|---|---|---|
| 101 | $Ph_3C$ | (1) | (2) | (2) | H | H | H | 1 | 2 | — | H | H | H | H | H |
| 102 | $Ph_3C$ | (1) | (2) | (2) | H | H | H | 1 | 2 | Ph | H | H | H | H | H |
| 103 | $Ph_3C$ | (1) | (2) | (2) | H | H | H | 1 | 2 | Ph | H | H | H | H | H |
| 104 | $Ph_3C$ | (1) | (2) | (2) | H | H | H | 1 | 2 | — | $CH_3$ | H | H | H | H |
| 105 | $Ph_3C$ | (1) | (2) | (2) | H | H | H | 1 | 2 | Ph | $CH_3$ | H | H | H | H |
| 106 | $Ph_3C$ | (1) | (2) | (2) | H | H | H | 1 | 2 | Ph | $CH_3$ | H | H | H | H |
| 107 | $Ph_3C$ | (1) | (2) | (2) | H | H | H | 1 | 2 | — | H | $CH_3$ | H | H | H |
| 108 | $Ph_3C$ | (1) | (2) | (2) | H | H | H | 1 | 2 | Ph | H | $CH_3$ | H | H | H |
| 109 | $Ph_3C$ | (1) | (2) | (2) | H | H | H | 1 | 2 | Ph | H | $CH_3$ | H | H | H |
| 110 | $Ph_3C$ | (1) | (2) | (2) | H | H | H | 1 | 2 | — | $CH_3$ | $CH_3$ | H | H | H |
| 111 | $Ph_3C$ | (1) | (2) | (2) | H | H | H | 1 | 2 | Ph | $CH_3$ | $CH_3$ | H | H | H |
| 112 | $Ph_3C$ | (1) | (2) | (2) | H | H | H | 1 | 2 | Ph | $CH_3$ | $CH_3$ | H | H | H |
| 113 | $Ph_3C$ | (1) | (2) | (2) | H | H | H | 1 | 2 | — | Ph1 | H | H | H | H |
| 114 | $Ph_3C$ | (1) | (2) | (2) | H | H | H | 1 | 2 | Ph | Ph1 | H | H | H | H |
| 115 | $Ph_3C$ | (1) | (2) | (2) | H | H | H | 1 | 2 | Ph | Ph1 | H | H | H | H |
| 116 | $Ph_3C$ | (1) | (2) | (2) | H | H | H | 1 | 2 | Ph | Ph1 | H | H | H | H |
| 117 | $Ph_3C$ | (1) | (2) | (2) | H | H | H | 1 | 2 | Ph | Ph1 | H | H | H | H |
| 118 | $Ph_3C$ | (1) | (2) | (2) | H | H | H | 1 | 2 | Ph | Ph1 | H | H | H | H |
| 119 | $Ph_3C$ | (1) | (2) | (2) | H | H | H | 1 | 2 | — | H | Ph1 | H | H | H |
| 120 | $Ph_3C$ | (1) | (2) | (2) | H | H | H | 1 | 2 | Ph | H | Ph1 | H | H | H |
| 121 | $Ph_3C$ | (1) | (2) | (2) | H | H | H | 1 | 2 | Ph | H | Ph1 | H | H | H |
| 122 | $Ph_3C$ | (1) | (2) | (2) | H | H | H | 1 | 2 | Ph | H | Ph1 | H | H | H |
| 123 | $Ph_3C$ | (1) | (2) | (2) | H | H | H | 1 | 2 | Ph | H | Ph1 | H | H | H |
| 124 | $Ph_3C$ | (1) | (2) | (2) | H | H | H | 1 | 2 | Ph | H | Ph1 | H | H | H |
| 125 | $Ph_3C$ | (1) | (2) | (2) | H | H | H | 1 | 2 | — | Ph1 | Ph1 | H | H | H |
| 126 | $Ph_3C$ | (1) | (2) | (2) | H | H | H | 1 | 2 | Ph | Ph1 | Ph1 | H | H | H |
| 127 | $Ph_3C$ | (1) | (2) | (2) | H | H | H | 1 | 2 | Ph | Ph1 | Ph1 | H | H | H |
| 128 | $Ph_3C$ | (1) | (2) | (2) | H | H | H | 1 | 2 | Ph | Ph1 | Ph1 | H | H | H |
| 129 | $Ph_3C$ | (1) | (2) | (2) | Ph | H | H | 1 | 2 | Ph | Ph1 | Ph1 | H | H | H |
| 130 | $Ph_3C$ | (1) | (2) | (2) | H | H | H | 1 | 2 | Np26 | Ph1 | Ph1 | H | H | H |

| No. | $R_6$ | $A_2$ | $R_7$ | $R_8$ | $R_9$ | $R_{10}$ | $R_{11}$ | $R_{12}$ | $R_{13}$ | $R_{14}$ | $R_{15}$ |
|---|---|---|---|---|---|---|---|---|---|---|---|
| 101 | H | — | H | H | H | H | H | H | H | H | H |
| 102 | H | — | H | H | H | H | H | H | H | H | H |
| 103 | H | Ph | H | H | H | H | H | H | H | H | H |
| 104 | H | — | H | H | H | H | H | H | H | H | H |
| 105 | H | — | H | H | H | H | H | H | H | H | H |
| 106 | H | Ph | H | H | H | H | H | H | H | H | H |
| 107 | H | — | H | H | H | H | H | H | H | H | H |
| 108 | H | — | H | H | H | H | H | H | H | H | H |
| 109 | H | Ph | H | H | H | H | H | H | H | H | H |
| 110 | H | — | H | H | H | H | H | H | H | H | H |
| 111 | H | — | H | H | H | H | H | H | H | H | H |
| 112 | H | Ph | H | H | H | H | H | H | H | H | H |
| 113 | H | — | H | H | H | H | H | H | H | H | H |

TABLE 5-continued

| | | | | | | | | | | | |
|---|---|---|---|---|---|---|---|---|---|---|---|
| 114 | H | — | H | H | H | H | H | H | H | H | H |
| 115 | H | Ph | H | H | H | H | H | H | H | H | H |
| 116 | H | — | H | H | H | H | H | H | H | H | CH3 |
| 117 | H | — | H | H | H | H | H | H | H | H | F |
| 118 | H | — | H | H | C2H5 | H | H | H | H | H | H |
| 119 | H | — | H | H | H | H | H | H | H | H | H |
| 120 | H | — | H | H | H | H | H | H | H | H | H |
| 121 | H | Ph | H | H | H | H | H | H | H | H | H |
| 122 | H | — | H | H | H | H | H | H | H | H | OCH3 |
| 123 | H | — | H | H | H | H | H | H | H | H | CF3 |
| 124 | H | — | H | H | H | H | H | H | H | H | Cl |
| 125 | H | — | H | H | H | H | H | H | H | H | H |
| 126 | H | — | H | H | H | H | H | H | H | H | H |
| 127 | H | Ph | H | H | H | H | H | H | H | H | H |
| 128 | H | — | H | H | CH3 | H | H | H | H | H | H |
| 129 | H | — | H | H | H | H | H | H | H | H | H |
| 130 | H | — | H | H | H | H | H | H | H | H | H |

TABLE 6

| No. | X | E | G | J | L | Ra | Rb | m | n | $A_1$ | $R_1$ | $R_2$ | $R_3$ | $R_4$ | $R_5$ |
|---|---|---|---|---|---|---|---|---|---|---|---|---|---|---|---|
| 131 | Ph4A | (1) | (1) | (1) | (2) | H | H | 3 | 1 | — | H | H | H | H | H |
| 132 | Ph4A | (1) | (1) | (1) | (2) | H | H | 3 | 1 | Ph | CH3 | Ph1 | H | H | H |
| 133 | Ph4A | (1) | (2) | (1) | (1) | H | H | 3 | 1 | — | H | CH3 | H | Ph1 | H |
| 134 | Ph4A | (1) | (2) | (1) | (1) | H | H | 2 | 2 | Ph | CH3 | CH3 | H | H | H |
| 135 | Ph4A | (1) | (2) | (1) | (2) | H | H | 2 | 2 | Ph | Ph1 | H | H | H | H |
| 136 | Ph4A | (1) | (2) | (1) | (2) | H | H | 2 | 2 | Ph | H | Ph1 | H | H | H |
| 137 | Ph4A | (1) | (2) | (2) | (1) | H | H | 2 | 2 | Ph | Ph1 | H | H | H | H |
| 138 | Ph4A | (1) | (2) | (2) | (1) | H | H | 2 | 2 | Ph | H | Ph1 | H | H | H |
| 139 | Ph4A | (1) | (2) | (2) | (2) | H | H | 1 | 3 | Ph | Ph1 | Ph1 | H | H | H |
| 140 | Ph4A | (2) | (2) | (1) | (2) | H | H | 1 | 3 | Np14 | Ph1 | H | H | H | H |
| 141 | Ph4B | (1) | (1) | (1) | (2) | H | H | 3 | 1 | — | H | H | H | H | H |
| 142 | Ph4B | (1) | (1) | (1) | (2) | H | H | 3 | 1 | Ph | CH3 | H | H | H | H |
| 143 | Ph4B | (1) | (2) | (1) | (1) | H | H | 3 | 1 | — | H | C3H7 | H | H | H |
| 144 | Ph4B | (1) | (2) | (1) | (1) | H | H | 2 | 2 | Ph | CH3 | CH3 | H | H | H |
| 145 | Ph4B | (1) | (2) | (1) | (2) | H | H | 2 | 2 | Ph | Ph1 | H | H | H | H |
| 146 | Ph4B | (1) | (2) | (1) | (2) | H | H | 2 | 2 | Ph | H | Ph1 | H | H | H |
| 147 | Ph4B | (1) | (2) | (2) | (1) | H | H | 2 | 2 | Ph | Ph1 | H | H | H | H |
| 148 | Ph4B | (1) | (2) | (2) | (1) | H | H | 2 | 2 | Ph | H | Ph1 | H | H | H |
| 149 | Ph4B | (1) | (2) | (2) | (2) | H | H | 1 | 3 | Ph | Ph1 | Ph1 | H | H | H |
| 150 | Ph4B | (2) | (2) | (1) | (2) | H | H | 1 | 3 | FL | Ph1 | H | H | H | H |

| No. | $R_6$ | $A_2$ | $R_7$ | $R_8$ | $R_9$ | $R_{10}$ | $R_{11}$ | $R_{12}$ | $R_{13}$ | $R_{14}$ | $R_{15}$ |
|---|---|---|---|---|---|---|---|---|---|---|---|
| 131 | H | — | H | H | H | H | H | H | H | H | H |
| 132 | H | — | H | H | H | H | H | H | H | H | OCH3 |
| 133 | H | Ph | H | H | H | H | H | H | H | H | CF3 |
| 134 | H | Ph | H | H | H | H | H | H | H | H | H |
| 135 | H | — | H | H | CH3 | H | H | H | H | H | H |
| 136 | H | — | H | H | H | H | H | H | H | H | F |
| 137 | H | — | H | H | H | H | H | H | H | H | H |
| 138 | H | Ph | H | H | H | H | H | H | H | H | H |
| 139 | H | Ph | H | H | H | H | H | H | H | H | H |
| 140 | H | — | H | H | H | H | H | H | H | H | H |
| 141 | H | — | H | H | H | H | H | H | H | H | H |
| 142 | H | — | H | H | C2H5 | H | H | H | H | H | H |
| 143 | H | Ph | H | H | H | H | H | H | H | H | H |
| 144 | H | Ph | H | H | H | H | H | H | H | H | H |
| 145 | H | — | H | H | H | H | H | H | H | H | H |
| 146 | H | — | H | H | H | H | H | H | H | H | H |
| 147 | H | — | H | H | H | H | H | H | H | H | H |
| 148 | H | Ph | H | H | H | H | H | H | H | H | H |
| 149 | H | Ph | H | H | H | H | H | H | H | H | H |
| 150 | H | — | H | H | H | H | H | H | H | H | H |

TABLE 7

| No. | X | E | G | J | L | Ra | Rb | m | n | $A_1$ | $R_1$ | $R_2$ | $R_3$ | $R_4$ |
|---|---|---|---|---|---|---|---|---|---|---|---|---|---|---|
| 151 | Ph4C | (1) | (2) | (1) | (2) | H | H | 2 | 2 | — | H | H | H | H |
| 152 | Ph4C | (1) | (2) | (1) | (2) | H | H | 2 | 2 | Ph | H | H | H | H |
| 153 | Ph4C | (1) | (2) | (1) | (2) | H | H | 2 | 2 | Ph | H | H | H | H |
| 154 | Ph4C | (1) | (2) | (1) | (2) | H | H | 2 | 2 | — | CH3 | H | H | H |

TABLE 7-continued

| No. | X | E | G | J | L | Ra | Rb | m | n | A₁ | R₁ | R₂ | R₃ | R₄ |
|---|---|---|---|---|---|---|---|---|---|---|---|---|---|---|
| 155 | Ph4C | (1) | (2) | (1) | (2) | H | H | 2 | 2 | Ph | CH3 | H | H | H |
| 156 | Ph4C | (1) | (2) | (1) | (2) | H | H | 2 | 2 | Ph | CH3 | H | H | H |
| 157 | Ph4C | (1) | (2) | (1) | (2) | H | H | 2 | 2 | — | H | CH3 | H | H |
| 158 | Ph4C | (1) | (2) | (1) | (2) | H | H | 2 | 2 | Ph | H | CH3 | H | H |
| 159 | Ph4C | (1) | (2) | (1) | (2) | H | H | 2 | 2 | Ph | H | CH3 | H | H |
| 160 | Ph4C | (1) | (2) | (1) | (2) | H | H | 2 | 2 | — | CH3 | CH3 | H | H |
| 161 | Ph4C | (1) | (2) | (1) | (2) | H | H | 2 | 2 | Ph | CH3 | CH3 | H | H |
| 162 | Ph4C | (1) | (2) | (1) | (2) | H | H | 2 | 2 | Ph | CH3 | CH3 | H | H |
| 163 | Ph4C | (1) | (2) | (1) | (2) | H | H | 2 | 2 | — | Ph1 | H | H | H |
| 164 | Ph4C | (1) | (2) | (1) | (2) | H | H | 2 | 2 | Ph | Ph1 | H | H | H |
| 165 | Ph4C | (1) | (2) | (1) | (2) | H | H | 2 | 2 | Ph | Ph1 | H | H | H |
| 166 | Ph4C | (1) | (2) | (1) | (2) | H | H | 2 | 2 | Ph | Ph1 | H | H | H |
| 167 | Ph4C | (1) | (2) | (1) | (2) | CH3 | CH3 | 2 | 2 | Ph | Ph1 | H | H | H |
| 168 | Ph4C | (1) | (2) | (1) | (2) | H | H | 2 | 2 | Ph | Ph1 | H | H | H |
| 169 | Ph4C | (1) | (2) | (1) | (2) | H | H | 2 | 2 | — | H | Ph1 | H | H |
| 170 | Ph4C | (1) | (2) | (1) | (2) | H | H | 2 | 2 | Ph | H | Ph1 | H | H |
| 171 | Ph4C | (1) | (2) | (1) | (2) | H | H | 2 | 2 | Ph | H | Ph1 | H | H |
| 172 | Ph4C | (1) | (2) | (1) | (2) | H | H | 2 | 2 | Ph | H | Ph1 | H | H |
| 173 | Ph4C | (1) | (2) | (1) | (2) | H | H | 2 | 2 | Ph | H | Ph1 | H | H |
| 174 | Ph4C | (1) | (2) | (1) | (2) | H | H | 2 | 2 | Ph | H | Ph1 | H | H |
| 175 | Ph4C | (1) | (2) | (1) | (2) | H | H | 2 | 2 | — | Ph1 | Ph1 | H | H |
| 176 | Ph4C | (1) | (2) | (1) | (2) | H | H | 2 | 2 | Ph | Ph1 | Ph1 | H | H |
| 177 | Ph4C | (1) | (2) | (1) | (2) | H | H | 2 | 2 | Ph | Ph1 | Ph1 | H | H |
| 178 | Ph4C | (1) | (2) | (1) | (2) | H | H | 2 | 2 | Ph | Ph1 | Ph1 | H | H |
| 179 | Ph4C | (1) | (2) | (1) | (2) | Ph | H | 2 | 2 | Ph | Ph1 | Ph1 | H | H |
| 180 | Ph4C | (1) | (2) | (1) | (2) | H | H | 2 | 2 | Np26 | Ph1 | Ph1 | H | H |

| No. | R₅ | R₆ | A₂ | R₇ | R₈ | R₉ | R₁₀ | R₁₁ | R₁₂ | R₁₃ | R₁₄ | R₁₅ |
|---|---|---|---|---|---|---|---|---|---|---|---|---|
| 151 | H | H | — | H | H | H | H | H | H | H | H | H |
| 152 | H | H | — | H | H | H | H | H | H | H | H | H |
| 153 | H | H | Ph | H | H | H | H | H | H | H | H | H |
| 154 | H | H | — | H | H | H | H | H | H | H | H | H |
| 155 | H | H | — | H | H | H | H | H | H | H | H | H |
| 156 | H | H | Ph | H | H | H | H | H | H | H | H | H |
| 157 | H | H | — | H | H | H | H | H | H | H | H | H |
| 158 | H | H | — | H | H | H | H | H | H | H | H | H |
| 159 | H | H | Ph | H | H | H | H | H | H | H | H | H |
| 160 | H | H | — | H | H | H | H | H | H | H | H | H |
| 161 | H | H | — | H | H | H | H | H | H | H | H | H |
| 162 | H | H | Ph | H | H | H | H | H | H | H | H | H |
| 163 | H | H | — | H | H | H | H | H | H | H | H | H |
| 164 | H | H | — | H | H | H | H | H | H | H | H | H |
| 165 | H | H | Ph | H | H | H | H | H | H | H | H | H |
| 166 | H | H | — | H | H | H | H | H | H | H | H | CH3 |
| 167 | H | H | — | H | H | H | H | H | H | H | H | F |
| 168 | H | H | — | H | H | C2H5 | H | H | H | H | H | H |
| 169 | H | H | — | H | H | H | H | H | H | H | H | H |
| 170 | H | H | — | H | H | H | H | H | H | H | H | H |
| 171 | H | H | Ph | H | H | H | H | H | H | H | H | H |
| 172 | H | H | — | H | H | H | H | H | H | H | H | OCH3 |
| 173 | H | H | — | H | H | H | H | H | H | H | H | CF3 |
| 174 | H | H | — | H | H | H | H | H | H | H | H | Cl |
| 175 | H | H | — | H | H | H | H | H | H | H | H | H |
| 176 | H | H | — | H | H | H | H | H | H | H | H | H |
| 177 | H | H | Ph | H | H | H | H | H | H | H | H | H |
| 178 | H | H | — | H | H | CH3 | H | H | H | H | H | H |
| 179 | H | H | — | H | H | H | H | H | H | H | H | H |
| 180 | H | H | — | H | H | H | H | H | H | H | H | H |

TABLE 8

| No. | X | E | G | J | L | Ra | Rb | m | n | A₁ | R₁ | R₂ | R₃ | R₄ | R₅ |
|---|---|---|---|---|---|---|---|---|---|---|---|---|---|---|---|
| 181 | Ph4C | (1) | (2) | (2) | (1) | H | H | 2 | 2 | — | H | H | H | H | H |
| 182 | Ph4C | (1) | (2) | (2) | (1) | H | H | 2 | 2 | Ph | H | H | H | H | H |
| 183 | Ph4C | (1) | (2) | (2) | (1) | H | H | 2 | 2 | Ph | H | H | H | H | H |
| 184 | Ph4C | (1) | (2) | (2) | (1) | H | H | 2 | 2 | — | CH3 | H | H | H | H |
| 185 | Ph4C | (1) | (2) | (2) | (1) | H | H | 2 | 2 | Ph | CH3 | H | H | H | H |
| 186 | Ph4C | (1) | (2) | (2) | (1) | H | H | 2 | 2 | Ph | CH3 | H | H | H | H |
| 187 | Ph4C | (1) | (2) | (2) | (1) | H | H | 2 | 2 | — | H | CH3 | H | H | H |
| 188 | Ph4C | (1) | (2) | (2) | (1) | H | H | 2 | 2 | Ph | H | CH3 | H | H | H |
| 189 | Ph4C | (1) | (2) | (2) | (1) | H | H | 2 | 2 | Ph | H | CH3 | H | H | H |
| 190 | Ph4C | (1) | (2) | (2) | (1) | H | H | 2 | 2 | — | CH3 | CH3 | H | H | H |
| 191 | Ph4C | (1) | (2) | (2) | (1) | H | H | 2 | 2 | Ph | CH3 | CH3 | H | H | H |
| 192 | Ph4C | (1) | (2) | (2) | (1) | H | H | 2 | 2 | Ph | CH3 | CH3 | H | H | H |

TABLE 8-continued

| No. | X | E | G | J | L | Ra | Rb | m | n | A₁ | R₁ | R₂ | R₃ | R₄ | R₅ |
|---|---|---|---|---|---|---|---|---|---|---|---|---|---|---|---|
| 193 | Ph4C | (1) | (2) | (2) | (1) | H | H | 2 | 2 | — | Ph1 | H | H | H | H |
| 194 | Ph4C | (1) | (2) | (2) | (1) | H | H | 2 | 2 | Ph | Ph1 | H | H | H | H |
| 195 | Ph4C | (1) | (2) | (2) | (1) | H | H | 2 | 2 | Ph | Ph1 | H | H | H | H |
| 196 | Ph4C | (1) | (2) | (2) | (1) | H | H | 2 | 2 | Ph | Ph1 | H | H | H | H |
| 197 | Ph4C | (1) | (2) | (2) | (1) | H | H | 2 | 2 | Ph | Ph1 | H | H | H | H |
| 198 | Ph4C | (1) | (2) | (2) | (1) | H | H | 2 | 2 | Ph | Ph1 | H | H | H | H |
| 199 | Ph4C | (1) | (2) | (2) | (1) | H | H | 2 | 2 | — | H | Ph1 | H | H | H |
| 200 | Ph4C | (1) | (2) | (2) | (1) | H | H | 2 | 2 | Ph | H | Ph1 | H | H | H |
| 201 | Ph4C | (1) | (2) | (2) | (1) | H | H | 2 | 2 | Ph | H | Ph1 | H | H | H |
| 202 | Ph4C | (1) | (2) | (2) | (1) | H | H | 2 | 2 | Ph | H | Ph1 | H | H | H |
| 203 | Ph4C | (1) | (2) | (2) | (1) | H | H | 2 | 2 | Ph | H | Ph1 | H | H | H |
| 204 | Ph4C | (1) | (2) | (2) | (1) | H | H | 2 | 2 | Ph | H | Ph1 | H | H | H |
| 205 | Ph4C | (1) | (2) | (2) | (1) | H | H | 2 | 2 | — | Ph1 | Ph1 | H | H | H |
| 206 | Ph4C | (1) | (2) | (2) | (1) | H | H | 2 | 2 | Ph | Ph1 | Ph1 | H | H | H |
| 207 | Ph4C | (1) | (2) | (2) | (1) | H | H | 2 | 2 | Ph | Ph1 | Ph1 | H | H | H |
| 208 | Ph4C | (1) | (2) | (2) | (1) | H | H | 2 | 2 | Ph | Ph1 | Ph1 | H | H | H |
| 209 | Ph4C | (1) | (2) | (2) | (1) | Ph | H | 2 | 2 | Ph | Ph1 | Ph1 | H | H | H |
| 210 | Ph4C | (1) | (2) | (2) | (1) | H | H | 2 | 2 | Np26 | Ph1 | Ph1 | H | H | H |

| No. | R₆ | A₂ | R₇ | R₈ | R₉ | R₁₀ | R₁₁ | R₁₂ | R₁₃ | R₁₄ | R₁₅ |
|---|---|---|---|---|---|---|---|---|---|---|---|
| 181 | H | — | H | H | H | H | H | H | H | H | H |
| 182 | H | — | H | H | FL2 | H | H | H | H | H | H |
| 183 | H | Ph | H | H | H | H | H | H | H | H | H |
| 184 | H | — | H | H | H | H | H | H | H | H | H |
| 185 | H | — | H | H | H | H | H | H | H | H | H |
| 186 | H | Ph | H | H | H | H | H | H | H | H | H |
| 187 | H | Qu | H | H | H | H | H | H | H | H | H |
| 188 | H | — | H | H | H | H | H | H | H | H | H |
| 189 | H | Ph | H | H | H | H | H | H | H | H | H |
| 190 | H | — | H | H | H | H | H | H | H | H | H |
| 191 | H | — | H | H | H | H | H | H | H | H | H |
| 192 | H | Ph | H | H | H | H | H | H | H | H | H |
| 193 | H | — | H | H | An9 | H | H | H | H | H | H |
| 194 | H | — | H | H | H | H | H | H | H | H | H |
| 195 | H | Ph | H | H | H | H | H | H | H | H | H |
| 196 | H | — | H | H | H | H | H | H | H | H | CH3 |
| 197 | H | — | H | H | H | H | H | H | H | H | F |
| 198 | H | — | H | H | C2H5 | H | H | H | H | H | H |
| 199 | H | Phen | H | H | H | H | H | H | H | H | H |
| 200 | H | — | H | H | H | H | H | H | H | H | H |
| 201 | H | Ph | H | H | H | H | H | H | H | H | H |
| 202 | H | — | H | H | H | H | H | H | H | H | OCH3 |
| 203 | H | — | H | H | H | H | H | H | H | H | CF3 |
| 204 | H | — | H | H | H | H | H | H | H | H | Cl |
| 205 | H | — | H | H | H | H | H | H | H | H | H |
| 206 | H | — | H | H | H | H | H | H | H | H | H |
| 207 | H | Ph | H | H | H | H | H | H | H | H | H |
| 208 | H | — | H | H | CH3 | H | H | H | H | H | H |
| 209 | H | — | H | H | H | H | H | H | H | H | H |
| 210 | H | — | H | H | H | H | H | H | H | H | H |

TABLE 9

| No. | X | E | G | J | L | Ra | Rb | m | n | A₁ | R₁ | R₂ | R₃ | R₄ | R₅ |
|---|---|---|---|---|---|---|---|---|---|---|---|---|---|---|---|
| 211 | Ph4C | (1) | (1) | (2) | (2) | H | H | 2 | 2 | — | H | H | H | H | H |
| 212 | Ph4C | (1) | (1) | (2) | (2) | H | H | 2 | 2 | Ph | H | H | H | H | H |
| 213 | Ph4C | (1) | (1) | (2) | (2) | H | H | 2 | 2 | Ph | H | H | H | H | H |
| 214 | Ph4C | (1) | (1) | (2) | (2) | H | H | 2 | 2 | — | CH3 | H | H | H | H |
| 215 | Ph4C | (1) | (1) | (2) | (2) | H | H | 2 | 2 | Ph | CH3 | H | H | H | H |
| 216 | Ph4C | (1) | (1) | (2) | (2) | H | H | 2 | 2 | Ph | CH3 | H | H | H | H |
| 217 | Ph4C | (1) | (1) | (2) | (2) | H | H | 2 | 2 | — | H | CH3 | H | H | H |
| 218 | Ph4C | (1) | (1) | (2) | (2) | H | H | 2 | 2 | Ph | H | CH3 | H | H | H |
| 219 | Ph4C | (1) | (1) | (2) | (2) | H | H | 2 | 2 | Ph | H | CH3 | H | H | H |
| 220 | Ph4C | (1) | (1) | (2) | (2) | H | H | 2 | 2 | — | CH3 | CH3 | H | H | H |
| 221 | Ph4C | (1) | (1) | (2) | (2) | H | H | 2 | 2 | Ph | CH3 | CH3 | H | H | H |
| 222 | Ph4C | (1) | (1) | (2) | (2) | H | H | 2 | 2 | Ph | CH3 | CH3 | H | H | H |
| 223 | Ph4C | (1) | (1) | (2) | (2) | H | H | 2 | 2 | — | Ph1 | H | H | H | H |
| 224 | Ph4C | (1) | (1) | (2) | (2) | H | H | 2 | 2 | Ph | Ph1 | H | H | H | H |
| 225 | Ph4C | (1) | (1) | (2) | (2) | H | H | 2 | 2 | Ph | Ph1 | H | H | H | H |
| 226 | Ph4C | (1) | (1) | (2) | (2) | H | H | 2 | 2 | Ph | Ph1 | H | H | H | H |
| 227 | Ph4C | (1) | (1) | (2) | (2) | H | H | 2 | 2 | Ph | Ph1 | H | H | H | H |
| 228 | Ph4C | (1) | (1) | (2) | (2) | H | H | 2 | 2 | Ph | Ph1 | H | H | H | H |
| 229 | Ph4C | (1) | (1) | (2) | (2) | H | H | 2 | 2 | — | H | Ph1 | H | H | H |
| 230 | Ph4C | (1) | (1) | (2) | (2) | H | H | 2 | 2 | Ph | H | Ph1 | H | H | H |

TABLE 9-continued

| No. | X | E | G | J | L | Ra | Rb | m | n | $A_1$ | $R_1$ | $R_2$ | $R_3$ | $R_4$ | $R_5$ |
|---|---|---|---|---|---|---|---|---|---|---|---|---|---|---|---|
| 231 | Ph4C | (1) | (1) | (2) | (2) | H | H | 2 | 2 | Ph | H | Ph1 | H | H | H |
| 232 | Ph4C | (1) | (1) | (2) | (2) | H | H | 2 | 2 | Ph | H | Ph1 | H | H | H |
| 233 | Ph4C | (1) | (1) | (2) | (2) | H | H | 2 | 2 | Ph | H | Ph1 | H | H | H |
| 234 | Ph4C | (1) | (1) | (2) | (2) | H | H | 2 | 2 | Ph | H | Ph1 | H | H | H |
| 235 | Ph4C | (1) | (1) | (2) | (2) | H | H | 2 | 2 | — | Ph1 | Ph1 | H | H | H |
| 236 | Ph4C | (1) | (1) | (2) | (2) | H | H | 2 | 2 | Ph | Ph1 | Ph1 | H | H | H |
| 237 | Ph4C | (1) | (1) | (2) | (2) | H | H | 2 | 2 | Ph | Ph1 | Ph1 | H | H | H |
| 238 | Ph4C | (1) | (1) | (2) | (2) | H | H | 2 | 2 | Ph | Ph1 | Ph1 | H | H | H |
| 239 | Ph4C | (1) | (1) | (2) | (2) | Ph | H | 2 | 2 | Ph | Ph1 | Ph1 | H | H | H |
| 240 | Ph4C | (1) | (1) | (2) | (2) | H | H | 2 | 2 | Np26 | Ph1 | Ph1 | H | H | H |

| No. | $R_6$ | $A_2$ | $R_7$ | $R_8$ | $R_9$ | $R_{10}$ | $R_{11}$ | $R_{12}$ | $R_{13}$ | $R_{14}$ | $R_{15}$ |
|---|---|---|---|---|---|---|---|---|---|---|---|
| 211 | H | — | H | H | H | H | H | H | H | H | H |
| 212 | H | — | H | H | H | H | H | H | H | H | H |
| 213 | H | Ph | H | H | H | H | H | H | H | H | H |
| 214 | H | — | H | H | H | H | H | H | H | H | H |
| 215 | H | — | H | H | H | H | H | H | H | H | H |
| 216 | H | Ph | H | H | H | H | H | H | H | H | H |
| 217 | H | — | H | H | H | H | H | H | H | H | H |
| 218 | H | — | H | H | H | H | H | H | H | H | H |
| 219 | H | Ph | H | H | H | H | H | H | H | H | H |
| 220 | H | — | H | H | H | H | H | H | H | H | H |
| 221 | H | — | H | H | H | H | H | H | H | H | H |
| 222 | H | Ph | H | H | H | H | H | H | H | H | H |
| 223 | H | — | H | H | H | H | H | H | H | H | Pn5 |
| 224 | H | — | H | H | H | H | H | H | H | H | H |
| 225 | H | Ph | H | H | H | H | H | H | H | H | H |
| 226 | H | — | H | H | H | H | H | H | H | H | CH3 |
| 227 | H | — | H | H | H | H | H | H | H | H | F |
| 228 | H | — | H | H | C2H5 | H | H | H | H | H | H |
| 229 | H | — | H | H | H | H | H | H | H | H | H |
| 230 | H | — | H | H | H | H | H | H | H | H | H |
| 231 | H | Ph | H | H | H | H | H | H | H | H | H |
| 232 | H | — | H | H | H | H | H | H | H | H | OCH3 |
| 233 | H | — | H | H | H | H | H | H | H | H | CF3 |
| 234 | H | — | H | H | H | H | H | H | H | H | Cl |
| 235 | H | — | H | H | Pr1 | H | H | H | H | H | H |
| 236 | H | — | H | H | H | H | H | H | H | H | H |
| 237 | H | Ph | H | H | H | H | H | H | H | H | H |
| 238 | H | — | H | H | CH3 | H | H | H | H | H | H |
| 239 | H | — | H | H | H | H | H | H | H | H | H |
| 240 | H | — | H | H | H | H | H | H | H | H | H |

TABLE 10

| No. | X | E | G | J | L | Ra | Rb | m | n | $A_1$ | $R_1$ | $R_2$ | $R_3$ | $R_4$ | $R_5$ | $R_6$ |
|---|---|---|---|---|---|---|---|---|---|---|---|---|---|---|---|---|
| 241 | Ph4C | (1) | (1) | (1) | (2) | H | H | 3 | 1 | — | CH3 | CH3 | H | H | H | H |
| 242 | Ph4C | (1) | (1) | (1) | (2) | H | H | 3 | 1 | Ph | CH3 | CH3 | H | H | H | H |
| 243 | Ph4C | (1) | (1) | (1) | (2) | H | H | 3 | 1 | Ph | CH3 | CH3 | H | H | H | H |
| 244 | Ph4C | (1) | (1) | (1) | (2) | H | H | 3 | 1 | — | Ph1 | H | H | H | H | H |
| 245 | Ph4C | (1) | (1) | (1) | (2) | H | H | 3 | 1 | Ph | Ph1 | H | H | H | H | H |
| 246 | Ph4C | (1) | (1) | (1) | (2) | H | H | 3 | 1 | Ph | Ph1 | H | H | H | H | H |
| 247 | Ph4C | (1) | (1) | (1) | (2) | H | H | 3 | 1 | Ph | Ph1 | H | H | H | H | H |
| 248 | Ph4C | (1) | (1) | (1) | (2) | H | H | 3 | 1 | Ph | Ph1 | H | H | H | H | H |
| 249 | Ph4C | (1) | (1) | (1) | (2) | H | H | 3 | 1 | Ph | H | Ph1 | H | H | H | H |
| 250 | Ph4C | (1) | (1) | (1) | (2) | H | H | 3 | 1 | Ph | H | Ph1 | H | H | H | H |
| 251 | Ph4C | (1) | (1) | (1) | (2) | H | H | 3 | 1 | — | Ph1 | Ph1 | H | H | H | H |
| 252 | Ph4C | (1) | (1) | (1) | (2) | H | H | 3 | 1 | Ph | Ph1 | Ph1 | H | H | H | H |
| 253 | Ph4C | (1) | (1) | (1) | (2) | H | H | 3 | 1 | Ph | Ph1 | Ph1 | H | H | H | H |
| 254 | Ph4C | (1) | (1) | (1) | (2) | H | H | 3 | 1 | Ph | Ph1 | Ph1 | H | H | H | H |
| 255 | Ph4C | (1) | (1) | (1) | (2) | Ph | H | 3 | 1 | Ph | Ph1 | Ph1 | H | H | H | H |
| 256 | Ph4C | (1) | (2) | (2) | (2) | H | H | 1 | 3 | — | CH3 | CH3 | H | H | H | H |
| 257 | Ph4C | (1) | (2) | (2) | (2) | H | H | 1 | 3 | Ph | CH3 | CH3 | H | H | H | H |
| 258 | Ph4C | (1) | (2) | (2) | (2) | H | H | 1 | 3 | Ph | CH3 | CH3 | H | H | H | H |
| 259 | Ph4C | (1) | (2) | (2) | (2) | H | H | 1 | 3 | — | Ph1 | H | H | H | H | H |
| 260 | Ph4C | (1) | (2) | (2) | (2) | H | H | 1 | 3 | Ph | Ph1 | H | H | H | H | H |
| 261 | Ph4C | (1) | (2) | (2) | (2) | H | H | 1 | 3 | Ph | Ph1 | H | H | H | H | H |
| 262 | Ph4C | (1) | (2) | (2) | (2) | H | H | 1 | 3 | Ph | Ph1 | H | H | H | H | H |
| 263 | Ph4C | (1) | (2) | (2) | (2) | H | H | 1 | 3 | Ph | Ph1 | H | H | H | H | H |
| 264 | Ph4C | (1) | (2) | (2) | (2) | H | H | 1 | 3 | Ph | H | Ph1 | H | H | H | H |
| 265 | Ph4C | (1) | (2) | (2) | (2) | H | H | 1 | 3 | Ph | H | Ph1 | H | H | H | H |
| 266 | Ph4C | (1) | (2) | (2) | (2) | H | H | 1 | 3 | — | Ph1 | Ph1 | H | H | H | H |
| 267 | Ph4C | (1) | (2) | (2) | (2) | H | H | 1 | 3 | Ph | Ph1 | Ph1 | H | H | H | H |

TABLE 10-continued

| | | | | | | | | | | | | | | | |
|---|---|---|---|---|---|---|---|---|---|---|---|---|---|---|---|
| 268 | Ph4C | (1) | (2) | (2) | (2) | H | H | 1 | 3 | Ph | Ph1 | Ph1 | H | H | H | H |
| 269 | Ph4C | (1) | (2) | (2) | (2) | H | H | 1 | 3 | Ph | Ph1 | Ph1 | H | H | H | H |
| 270 | Ph4C | (1) | (2) | (2) | (2) | Ph | H | 1 | 3 | Ph | Ph1 | Ph1 | H | H | H | H |

| No. | $A_2$ | $R_7$ | $R_8$ | $R_9$ | $R_{10}$ | $R_{11}$ | $R_{12}$ | $R_{13}$ | $R_{14}$ | $R_{15}$ |
|---|---|---|---|---|---|---|---|---|---|---|
| 241 | — | H | H | H | H | H | H | H | H | H |
| 242 | — | H | H | H | H | H | H | H | H | H |
| 243 | Ph | H | H | H | H | H | H | H | H | H |
| 244 | — | H | H | H | H | H | H | H | H | H |
| 245 | — | H | H | H | H | H | H | H | H | H |
| 246 | Ph | H | H | H | H | H | H | H | H | H |
| 247 | — | H | H | H | H | H | H | H | H | CH3 |
| 248 | — | H | H | H | H | H | H | H | H | F |
| 249 | — | H | H | H | H | H | H | H | H | CF3 |
| 250 | — | H | H | H | H | H | H | H | H | Cl |
| 251 | — | H | H | H | H | H | H | H | H | H |
| 252 | — | H | H | H | H | H | H | H | H | H |
| 253 | Ph | H | H | H | H | H | H | H | H | H |
| 254 | — | H | H | CH3 | H | H | H | H | H | H |
| 255 | — | H | H | H | H | H | H | H | H | H |
| 256 | — | H | H | H | H | H | H | H | H | H |
| 257 | — | H | H | H | H | H | H | H | H | H |
| 258 | Ph | H | H | H | H | H | H | H | H | H |
| 259 | — | H | H | Phen9 | H | H | H | H | H | H |
| 260 | — | H | H | H | H | H | H | H | H | H |
| 261 | Ph | H | H | H | H | H | H | H | H | H |
| 262 | — | H | H | H | H | H | H | H | H | CH3 |
| 263 | — | H | H | H | H | H | H | H | H | F |
| 264 | — | H | H | H | H | H | H | H | H | CF3 |
| 265 | — | H | H | H | H | H | H | H | H | Cl |
| 266 | — | H | H | H | H | H | H | H | H | H |
| 267 | — | H | H | H | H | H | H | H | H | H |
| 268 | Ph | H | H | H | H | H | H | H | H | H |
| 269 | — | H | H | CH3 | H | H | H | H | H | H |
| 270 | — | H | H | H | H | H | H | H | H | H |

TABLE 11

| No. | X | E | G | J | L | M | Q | Ra | m | n | $A_1$ | $R_1$ | $R_2$ | $R_3$ | $R_4$ |
|---|---|---|---|---|---|---|---|---|---|---|---|---|---|---|---|
| 271 | Ph5 | (1) | (1) | (1) | (1) | (2) | — | H | 4 | 1 | — | H | H | H | H |
| 272 | Ph5 | (1) | (1) | (1) | (2) | (1) | — | H | 4 | 1 | Ph | CH3 | Ph1 | H | H |
| 273 | Ph5 | (1) | (1) | (2) | (1) | (1) | — | H | 4 | 1 | — | H | CH3 | H | Ph1 |
| 274 | Ph5 | (1) | (1) | (1) | (2) | (2) | — | H | 3 | 2 | Ph | CH3 | CH3 | H | H |
| 275 | Ph5 | (1) | (1) | (2) | (1) | (2) | — | H | 3 | 2 | Ph | Ph1 | H | H | H |
| 276 | Ph5 | (1) | (2) | (1) | (1) | (2) | — | H | 3 | 2 | Ph | H | Ph1 | H | H |
| 277 | Ph5 | (2) | (1) | (1) | (1) | (2) | — | H | 3 | 2 | Ph | Ph1 | Ph1 | H | H |
| 278 | Ph5 | (1) | (1) | (2) | (2) | (2) | — | H | 2 | 3 | Ph | H | Ph1 | H | H |
| 279 | Ph5 | (1) | (2) | (1) | (2) | (2) | — | H | 2 | 3 | Ph | Ph1 | Ph1 | H | H |
| 280 | Ph5 | (2) | (2) | (1) | (1) | (2) | — | H | 2 | 3 | Np14 | Ph1 | H | H | H |
| 281 | Ph6 | (1) | (1) | (1) | (1) | (1) | (2) | — | 5 | 1 | — | H | H | H | H |
| 282 | Ph6 | (1) | (1) | (1) | (2) | (1) | — | 5 | 1 | Ph | CH3 | H | H | H |
| 283 | Ph6 | (1) | (1) | (2) | (1) | (1) | (1) | — | 5 | 1 | — | H | C3H7 | H | H |
| 284 | Ph6 | (1) | (1) | (1) | (2) | (2) | — | 4 | 2 | Ph | CH3 | CH3 | H | H |
| 285 | Ph6 | (1) | (1) | (2) | (1) | (2) | — | 4 | 2 | Ph | Ph1 | H | H | H |
| 286 | Ph6 | (1) | (2) | (1) | (1) | (2) | — | 4 | 2 | Ph | H | Ph1 | H | H |
| 287 | Ph6 | (1) | (2) | (1) | (1) | (2) | — | 4 | 2 | Ph | Ph1 | Ph1 | H | H |
| 288 | Ph6 | (1) | (1) | (2) | (2) | (2) | — | 3 | 3 | Ph | H | Ph1 | H | H |
| 289 | Ph6 | (1) | (2) | (2) | (1) | (2) | — | 3 | 3 | Ph | Ph1 | Ph1 | H | H |
| 290 | Ph6 | (1) | (2) | (2) | (1) | (1) | (2) | — | 3 | 3 | FL | Ph1 | H | H | H |

| No. | $R_5$ | $R_6$ | $A_2$ | $R_7$ | $R_8$ | $R_9$ | $R_{10}$ | $R_{11}$ | $R_{12}$ | $R_{13}$ | $R_{14}$ | $R_{15}$ |
|---|---|---|---|---|---|---|---|---|---|---|---|---|
| 271 | H | H | — | H | H | H | H | H | H | H | H | H |
| 272 | H | H | — | H | H | H | H | H | H | H | H | OCH3 |
| 273 | H | H | Ph | H | H | H | H | H | H | H | H | CF3 |
| 274 | H | H | Ph | H | H | H | H | H | H | H | H | H |
| 275 | H | H | — | H | H | CH3 | H | H | H | H | H | H |
| 276 | H | H | — | H | H | H | H | H | H | H | H | F |
| 277 | H | H | — | H | H | H | H | H | H | H | H | H |
| 278 | H | H | Ph | H | H | H | H | H | H | H | H | H |
| 279 | H | H | Ph | H | H | H | H | H | H | H | H | H |
| 280 | H | H | — | H | H | H | H | H | H | H | H | H |
| 281 | H | H | — | H | H | Np2 | H | H | H | H | H | H |
| 282 | H | H | — | H | H | C2H5 | H | H | H | H | H | H |

TABLE 11-continued

| | | | | | | | | | | | | |
|---|---|---|---|---|---|---|---|---|---|---|---|---|
| 283 | H | H | Ph | H | H | H | H | H | H | H | H | H |
| 284 | H | H | Ph | H | H | H | H | H | H | H | H | H |
| 285 | H | H | — | H | H | H | H | H | H | H | H | H |
| 286 | H | H | — | H | H | H | H | H | H | H | H | H |
| 287 | H | H | — | H | H | H | H | H | H | H | H | H |
| 288 | H | H | Ph | H | H | H | H | H | H | H | H | Np1 |
| 289 | H | H | Ph | H | H | H | H | H | H | H | H | H |
| 290 | H | H | — | H | H | H | H | H | H | H | H | H |

TABLE 12

| No. | X | E | G | Ra | Rb | Rc | m | n | A$_1$ | R$_1$ | R$_2$ | R$_3$ | R$_4$ | R$_5$ | R$_6$ |
|---|---|---|---|---|---|---|---|---|---|---|---|---|---|---|---|
| 291 | Pi2A | (1) | (2) | H | H | H | 1 | 1 | — | H | H | H | H | H | H |
| 292 | Pi2A | (1) | (2) | H | H | H | 1 | 1 | Ph | CH3 | Ph1 | H | H | H | H |
| 293 | Pi2A | (1) | (2) | H | H | H | 1 | 1 | — | H | CH3 | H | Ph1 | H | H |
| 294 | Pi2A | (1) | (2) | H | H | H | 1 | 1 | Ph | CH3 | CH3 | H | H | H | H |
| 295 | Pi2A | (1) | (2) | H | H | H | 1 | 1 | Ph | Ph1 | H | H | H | H | H |
| 296 | Pi2B | (1) | (2) | H | H | H | 1 | 1 | Ph | H | Ph1 | H | H | H | H |
| 297 | Pi2B | (1) | (2) | H | H | H | 1 | 1 | Ph | Ph1 | Ph1 | H | H | H | H |
| 298 | Pi2B | (1) | (2) | H | H | H | 1 | 1 | Ph | Ph1 | H | H | H | H | H |
| 299 | Pi2B | (1) | (2) | H | H | H | 1 | 1 | Ph | Ph1 | Ph1 | H | H | H | H |
| 300 | Pi2B | (1) | (2) | H | H | H | 1 | 1 | Np14 | Ph1 | H | H | H | H | H |
| 301 | Pi2C | (1) | (2) | H | H | H | 1 | 1 | — | H | H | H | H | H | H |
| 302 | Pi2C | (1) | (2) | H | H | H | 1 | 1 | Ph | CH3 | H | H | H | H | H |
| 303 | Pi2C | (1) | (2) | H | H | H | 1 | 1 | — | H | C3H7 | H | H | H | H |
| 304 | Pi2C | (1) | (2) | H | H | H | 1 | 1 | Ph | CH3 | CH3 | H | H | H | H |
| 305 | Pi2C | (1) | (2) | H | H | H | 1 | 1 | Ph | Ph1 | FL2 | H | H | H | H |
| 306 | Pi2D | (1) | (2) | H | H | H | 1 | 1 | Ph | H | Ph1 | H | H | H | H |
| 307 | Pi2D | (1) | (2) | H | H | H | 1 | 1 | Ph | Ph1 | Ph1 | H | H | H | H |
| 308 | Pi2D | (1) | (2) | H | H | H | 1 | 1 | Ph | H | Ph1 | H | H | H | H |
| 309 | Pi2D | (1) | (2) | H | H | H | 1 | 1 | Ph | Ph1 | Ph1 | H | H | H | H |
| 310 | Pi2D | (1) | (2) | H | H | H | 1 | 1 | FL | Ph1 | H | H | H | H | H |

| No. | A$_2$ | R$_7$ | R$_8$ | R$_9$ | R$_{10}$ | R$_{11}$ | R$_{12}$ | R$_{13}$ | R$_{14}$ | R$_{15}$ |
|---|---|---|---|---|---|---|---|---|---|---|
| 291 | — | H | H | H | H | H | H | H | H | H |
| 292 | — | H | H | H | H | H | H | H | H | OCH3 |
| 293 | Ph | H | H | H | H | H | H | H | H | CF3 |
| 294 | Ph | H | H | H | H | H | H | H | H | H |
| 295 | — | H | H | CH3 | H | H | H | H | H | H |
| 296 | — | H | H | H | H | H | H | H | H | F |
| 297 | — | H | H | H | H | H | H | H | H | H |
| 298 | Ph | H | H | H | H | H | H | H | H | OCF3 |
| 299 | Ph | H | H | H | H | H | H | H | H | H |
| 300 | — | H | H | H | H | H | H | H | H | H |
| 301 | — | H | H | H | H | H | H | H | H | H |
| 302 | — | H | H | C2H5 | H | H | H | H | H | H |
| 303 | Ph | H | H | H | H | H | H | H | H | H |
| 304 | Ph | H | H | H | H | H | H | H | H | H |
| 305 | — | H | H | H | H | H | H | H | H | H |
| 306 | — | H | H | H | H | H | H | H | H | H |
| 307 | — | H | H | H | H | H | H | H | H | H |
| 308 | Ph | H | H | H | H | H | H | H | H | H |
| 309 | Ph | H | H | H | H | H | H | H | H | H |
| 310 | — | H | H | H | H | H | H | H | H | OC2H5 |

TABLE 13

| No. | X | E | G | Ra | Rb | m | n | A$_1$ | R$_1$ | R$_2$ | R$_3$ | R$_4$ | R$_5$ | R$_6$ |
|---|---|---|---|---|---|---|---|---|---|---|---|---|---|---|
| 311 | Pd2A | (1) | (2) | H | H | 1 | 1 | — | H | H | H | H | H | H |
| 312 | Pd2A | (1) | (2) | H | H | 1 | 1 | Ph | CH3 | Ph1 | H | H | H | H |
| 313 | Pd2A | (1) | (2) | H | H | 1 | 1 | — | H | CH3 | H | Ph1 | H | H |
| 314 | Pz2A | (1) | (2) | H | H | 1 | 1 | Ph | CH3 | CH3 | H | H | H | H |
| 315 | Pz2A | (1) | (2) | H | H | 1 | 1 | Ph | Ph1 | H | H | H | H | H |
| 316 | Pz2A | (1) | (2) | H | H | 1 | 1 | Ph | H | Ph1 | H | H | H | H |
| 317 | Pz2B | (1) | (2) | H | H | 1 | 1 | Ph | Ph1 | Ph1 | H | H | H | H |
| 318 | Pz2B | (1) | (2) | H | H | 1 | 1 | Ph | Ph1 | H | H | H | H | H |
| 319 | Pz2B | (1) | (2) | H | H | 1 | 1 | Ph | Ph1 | Ph1 | H | H | H | H |
| 320 | Pz2B | (1) | (2) | H | H | 1 | 1 | Np14 | Ph1 | H | H | H | H | H |
| 321 | Pd2B | (1) | (2) | H | H | 1 | 1 | — | H | H | H | H | H | H |
| 322 | Pd2B | (1) | (2) | H | H | 1 | 1 | Ph | CH3 | H | H | H | H | H |
| 323 | Pd2B | (1) | (2) | H | H | 1 | 1 | — | H | C3H7 | H | H | H | H |

TABLE 13-continued

| | | | | | | | | | | | | | |
|---|---|---|---|---|---|---|---|---|---|---|---|---|---|
| 324 | Pd2B | (1) | (2) | H | H | 1 | 1 | Ph | CH3 | CH3 | H | H | H | H |
| 325 | Pz2C | (1) | (2) | H | H | 1 | 1 | Ph | Ph1 | H | H | H | H | H |
| 326 | Pz2C | (1) | (2) | H | H | 1 | 1 | Ph | H | Ph1 | H | H | H | H |
| 327 | Pz2C | (1) | (2) | H | H | 1 | 1 | Ph | Ph1 | Ph1 | H | H | H | H |
| 328 | Pm2A | (1) | (2) | H | H | 1 | 1 | Ph | H | Ph1 | H | H | H | H |
| 329 | Pm2A | (1) | (2) | H | H | 1 | 1 | Ph | Ph1 | Ph1 | H | H | H | H |
| 330 | Pm2A | (1) | (2) | H | H | 1 | 1 | FL | Ph1 | H | H | H | H | H |

| No. | $A_2$ | $R_7$ | $R_8$ | $R_9$ | $R_{10}$ | $R_{11}$ | $R_{12}$ | $R_{13}$ | $R_{14}$ | $R_{15}$ |
|---|---|---|---|---|---|---|---|---|---|---|
| 311 | — | H | H | H | H | H | H | H | H | H |
| 312 | — | H | H | H | H | H | H | H | H | OCH3 |
| 313 | Ph | H | H | H | H | H | H | H | H | CF3 |
| 314 | Ph | H | H | H | H | H | H | H | H | H |
| 315 | — | H | H | CH3 | H | H | H | H | H | H |
| 316 | — | H | H | H | H | H | H | H | H | F |
| 317 | — | H | H | H | H | H | H | H | H | H |
| 318 | Ph | H | H | H | H | H | H | H | H | H |
| 319 | Ph | H | H | H | H | H | H | H | H | H |
| 320 | — | H | H | H | H | H | H | H | H | H |
| 321 | — | H | H | H | H | H | H | H | H | H |
| 322 | — | H | H | C2H5 | H | H | H | H | H | H |
| 323 | Ph | H | H | H | H | H | H | H | H | H |
| 324 | Th | H | H | H | H | H | H | H | H | H |
| 325 | — | H | H | H | H | H | H | H | H | H |
| 326 | — | H | H | H | H | H | H | H | H | H |
| 327 | — | H | H | H | H | H | H | H | H | H |
| 328 | Ph | H | H | H | H | H | H | H | H | C(CH3)3 |
| 329 | Ph | H | H | H | H | H | H | H | H | H |
| 330 | — | H | H | H | H | H | H | H | H | H |

TABLE 14

| No. | X | E | G | Ra | m | n | $A_1$ | $R_1$ | $R_2$ | $R_3$ | $R_4$ | $R_5$ | $R_6$ | $A_2$ | $R_7$ | $R_8$ | $R_9$ | $R_{10}$ | $R_{11}$ | $R_{12}$ | $R_{13}$ | $R_{14}$ | $R_{15}$ |
|---|---|---|---|---|---|---|---|---|---|---|---|---|---|---|---|---|---|---|---|---|---|---|---|
| 331 | Tr2A | (1) | (2) | H | 1 | 1 | — | H | H | H | H | H | H | BPh | H | H | H | H | H | H | H | H | H |
| 332 | Tr2A | (1) | (2) | H | 1 | 1 | Ph | CH3 | Ph1 | H | H | H | H | — | H | H | H | H | H | H | H | H | OCH3 |
| 333 | Tr2A | (1) | (2) | H | 1 | 1 | — | H | CH3 | H | Ph1 | H | H | Ph | H | H | H | H | H | H | H | H | CF3 |
| 334 | Tr2A | (1) | (2) | H | 1 | 1 | Ph | CH3 | CH3 | H | H | H | H | Ph | H | H | H | H | H | H | H | H | H |
| 335 | Tr2B | (1) | (2) | H | 1 | 1 | Ph | Ph1 | H | H | H | H | H | — | H | H | CH3 | H | H | H | H | H | H |
| 336 | Tr2B | (1) | (2) | H | 1 | 1 | Ph | H | Ph1 | H | H | H | H | — | H | H | H | H | H | H | H | H | F |
| 337 | Tr2B | (1) | (2) | H | 1 | 1 | Ph | Ph1 | Ph1 | H | H | H | H | — | H | H | H | H | H | H | H | H | H |
| 338 | Tr2B | (1) | (2) | H | 1 | 1 | Ph | Ph1 | H | H | H | H | H | Ph | H | H | H | H | H | H | H | H | H |
| 339 | Te2A | (1) | (2) | — | 1 | 1 | Ph | Ph1 | Ph1 | H | H | H | H | Ph | H | H | H | H | H | H | H | H | H |
| 340 | Te2A | (1) | (2) | — | 1 | 1 | Np14 | Ph1 | H | H | H | H | H | — | H | H | H | H | H | H | H | H | H |

TABLE 15

| No. | X | E | G | J | Ra | Rb | m | n | $A_1$ | $R_1$ | $R_2$ | $R_3$ | $R_4$ | $R_5$ | $R_6$ |
|---|---|---|---|---|---|---|---|---|---|---|---|---|---|---|---|
| 341 | Pi3A | (1) | (1) | (2) | H | H | 2 | 1 | — | H | H | H | H | H | H |
| 342 | Pi3A | (1) | (1) | (2) | H | H | 2 | 1 | Ph | CH3 | Ph1 | H | H | H | H |
| 343 | Pi3A | (1) | (1) | (2) | H | H | 2 | 1 | — | Ph1 | CH3 | H | H | H | H |
| 344 | Pi3A | (1) | (1) | (2) | H | H | 2 | 1 | Ph | CH3 | CH3 | H | H | H | H |
| 345 | Pd3A | (1) | (2) | (1) | H | — | 2 | 1 | Ph | Ph1 | H | H | H | H | H |
| 346 | Pd3A | (1) | (2) | (1) | H | — | 2 | 1 | Ph | H | Ph1 | H | H | H | H |
| 347 | Pd3A | (2) | (2) | (1) | H | — | 1 | 2 | Ph | Ph1 | Ph1 | H | H | H | H |
| 348 | Pd3A | (2) | (2) | (1) | H | — | 1 | 2 | Ph | Ph1 | Ph1 | H | H | H | H |
| 349 | Pi3B | (2) | (1) | (2) | H | H | 1 | 2 | Ph | Ph1 | Ph1 | H | H | H | H |
| 350 | Pi3B | (2) | (1) | (2) | H | H | 1 | 2 | Np14 | Ph1 | H | H | H | H | H |
| 351 | Pi3B | (1) | (1) | (2) | H | H | 2 | 1 | — | H | H | H | H | H | H |
| 352 | Pi3B | (1) | (1) | (2) | H | H | 2 | 1 | Ph | CH3 | H | H | H | H | H |
| 353 | Pz3B | (1) | (1) | (2) | H | — | 2 | 1 | — | H | C3H7 | H | H | H | H |
| 354 | Pz3B | (1) | (2) | (1) | H | — | 2 | 1 | Ph | CH3 | CH3 | H | H | H | H |
| 355 | Pz3B | (1) | (2) | (1) | H | — | 2 | 1 | Ph | Ph1 | H | H | H | H | H |
| 356 | Pz3B | (1) | (2) | (1) | H | — | 2 | 1 | Np15 | H | Ph1 | H | H | H | H |
| 357 | Pi3C | (2) | (2) | (1) | H | H | 1 | 2 | Ph | Ph1 | Ph1 | H | H | H | H |
| 358 | Pi3C | (2) | (2) | (1) | H | H | 1 | 2 | Ph | H | Ph1 | H | H | H | H |
| 359 | Pi3C | (2) | (1) | (2) | H | H | 1 | 2 | Ph | Ph1 | Ph1 | H | H | H | H |
| 360 | Pi3C | (2) | (1) | (2) | H | H | 1 | 2 | FL | Ph1 | H | H | H | H | H |

TABLE 15-continued

| No. | A₂ | R₇ | R₈ | R₉ | R₁₀ | R₁₁ | R₁₂ | R₁₃ | R₁₄ | R₁₅ |
|---|---|---|---|---|---|---|---|---|---|---|
| 341 | — | H | H | H | H | H | H | H | H | H |
| 342 | — | H | H | H | H | H | H | H | H | OCH3 |
| 343 | Ph | H | H | H | H | H | H | H | H | CF3 |
| 344 | Ph | H | H | H | H | H | H | H | H | H |
| 345 | — | H | H | CH3 | H | H | H | H | H | H |
| 346 | — | H | H | H | H | H | H | H | H | F |
| 347 | — | H | H | H | H | H | H | H | H | H |
| 348 | Ph | H | H | H | H | H | H | H | H | H |
| 349 | Ph | H | H | H | H | H | H | H | H | H |
| 350 | — | H | H | H | H | H | H | H | H | H |
| 351 | Np15 | H | H | H | H | H | H | H | H | H |
| 352 | — | H | H | C2H5 | H | H | H | H | H | H |
| 353 | Ph | H | H | H | H | H | H | H | H | H |
| 354 | Ph | H | H | H | H | H | H | H | H | H |
| 355 | — | H | H | H | H | H | H | H | H | H |
| 356 | — | H | H | H | H | H | H | H | H | OCF3 |
| 357 | Np26 | H | H | H | H | H | H | H | H | H |
| 358 | Ph | H | H | H | H | H | H | H | H | H |
| 359 | Ph | H | H | H | H | H | H | H | H | H |
| 360 | — | H | H | H | H | H | H | H | H | H |

TABLE 16

| No. | X | E | G | J | m | n | A₁ | R₁ | R₂ | R₃ | R₄ | R₅ | R₆ | A₂ | R₇ | R₈ | R₉ | R₁₀ | R₁₁ | R₁₂ | R₁₃ | R₁₄ | R₁₅ |
|---|---|---|---|---|---|---|---|---|---|---|---|---|---|---|---|---|---|---|---|---|---|---|---|
| 361 | Tr3A | (1) | (1) | (2) | 2 | 1 | Ph | Ph1 | H | H | H | H | H | Ph | H | H | H | H | H | H | H | H | H |
| 362 | Tr3A | (1) | (1) | (2) | 2 | 1 | Ph | Ph1 | H | H | H | H | H | — | H | H | H | H | H | H | H | H | CH3 |
| 363 | Tr3A | (1) | (1) | (2) | 2 | 1 | Ph | Ph1 | H | H | H | H | H | — | H | H | H | H | H | H | H | H | F |
| 364 | Tr3A | (1) | (1) | (2) | 2 | 1 | Ph | Ph1 | H | H | H | H | H | — | H | H | C2H5 | H | H | H | H | H | H |
| 365 | Tr3A | (1) | (1) | (2) | 2 | 1 | — | H | Ph1 | H | H | H | H | Pi | H | H | H | H | H | H | H | H | H |
| 366 | Tr3A | (1) | (1) | (2) | 2 | 1 | Ph | H | Ph1 | H | H | H | H | — | H | H | H | H | H | H | H | H | H |
| 367 | Tr3A | (1) | (1) | (2) | 2 | 1 | Ph | Ph1 | H | H | H | H | H | Ph | H | H | H | H | H | H | H | H | H |
| 368 | Tr3A | (1) | (1) | (2) | 2 | 1 | Ph | H | Ph1 | H | H | H | H | — | H | H | H | H | H | H | H | H | OCH3 |
| 369 | Tr3A | (1) | (1) | (2) | 2 | 1 | Ph | H | Ph1 | H | H | H | H | — | H | H | H | H | H | H | H | H | CF3 |
| 370 | Tr3A | (1) | (1) | (2) | 2 | 1 | — | Ph1 | Ph1 | H | H | H | H | — | H | H | H | H | H | H | H | H | H |
| 371 | Tr3A | (1) | (1) | (2) | 2 | 1 | Ph | Ph1 | Ph1 | H | H | H | H | — | H | H | H | H | H | H | H | H | H |
| 372 | Tr3A | (1) | (1) | (2) | 2 | 1 | Ph | Ph1 | Ph1 | H | H | H | H | Ph | H | H | H | H | H | H | H | H | OCH2C3F7 |
| 373 | Tr3A | (1) | (1) | (2) | 2 | 1 | Ph | Ph1 | Ph1 | H | H | H | H | — | H | H | CH3 | H | H | H | H | H | H |
| 374 | Tr3A | (1) | (1) | (2) | 2 | 1 | Ph | Ph1 | Ph1 | H | H | H | H | — | H | H | H | H | H | H | H | H | H |
| 375 | Tr3A | (1) | (1) | (2) | 2 | 1 | Np26 | Ph1 | Ph1 | H | H | H | H | — | H | H | H | H | H | H | H | H | H |
| 376 | Tr3A | (1) | (2) | (2) | 1 | 2 | Ph | Ph1 | H | H | H | H | H | Ph | H | H | H | H | H | H | H | H | H |
| 377 | Tr3A | (1) | (2) | (2) | 1 | 2 | Ph | Ph1 | H | H | H | H | H | — | H | H | H | H | H | H | H | H | CH3 |
| 378 | Tr3A | (1) | (2) | (2) | 1 | 2 | Ph | Ph1 | H | H | H | H | H | — | H | H | H | H | H | H | H | H | F |
| 379 | Tr3A | (1) | (2) | (2) | 1 | 2 | Ph | Ph1 | H | H | H | H | H | — | H | H | C2H5 | H | H | H | H | H | H |
| 380 | Tr3A | (1) | (2) | (2) | 1 | 2 | — | H | Ph1 | H | H | H | H | Qu | H | H | H | H | H | H | H | H | H |
| 381 | Tr3A | (1) | (2) | (2) | 1 | 2 | Ph | H | Ph1 | H | H | H | H | — | H | H | H | H | H | H | H | H | H |
| 382 | Tr3A | (1) | (2) | (2) | 1 | 2 | Ph | Ph1 | H | H | H | H | H | Ph | H | H | H | H | H | H | H | H | H |
| 383 | Tr3A | (1) | (2) | (2) | 1 | 2 | Ph | H | Ph1 | H | H | H | H | — | H | H | H | H | H | H | H | H | OCH3 |
| 384 | Tr3A | (1) | (2) | (2) | 1 | 2 | Ph | H | Ph1 | H | H | H | H | — | H | H | H | H | H | H | H | H | CF3 |
| 385 | Tr3A | (1) | (2) | (2) | 1 | 2 | Ph | H | Ph1 | H | H | H | H | — | H | H | H | H | H | H | H | H | Cl |
| 386 | Tr3A | (1) | (2) | (2) | 1 | 2 | — | Ph1 | Ph1 | H | H | H | H | An | H | H | H | H | H | H | H | H | H |
| 387 | Tr3A | (1) | (2) | (2) | 1 | 2 | Ph | Ph1 | Ph1 | H | H | H | H | — | H | H | H | H | H | H | H | H | H |
| 388 | Tr3A | (1) | (2) | (2) | 1 | 2 | Ph | Ph1 | Ph1 | H | H | H | H | Ph | H | H | H | H | H | H | H | H | H |
| 389 | Tr3A | (1) | (2) | (2) | 1 | 2 | Ph | Ph1 | Ph1 | H | H | H | H | — | H | H | CH3 | H | H | H | H | H | H |
| 390 | Tr3A | (1) | (2) | (2) | 1 | 2 | Ph | Ph1 | Ph1 | H | H | H | H | — | H | H | H | H | H | H | H | H | H |

TABLE 17

| No. | X | E | G | J | L | Ra | m | n | A₁ | R₁ | R₂ | R₃ | R₄ | R₅ | R₆ |
|---|---|---|---|---|---|---|---|---|---|---|---|---|---|---|---|
| 391 | Pd4A | (1) | (1) | (1) | (2) | — | 3 | 1 | — | H | H | H | H | H | H |
| 392 | Pd4A | (1) | (1) | (1) | (2) | — | 3 | 1 | Ph | CH3 | Ph1 | H | H | H | H |
| 393 | Pd4A | (1) | (2) | (1) | (1) | — | 3 | 1 | — | H | CH3 | H | Ph1 | H | H |
| 394 | Pd4A | (1) | (2) | (1) | (1) | — | 2 | 2 | Ph | CH3 | CH3 | H | H | H | H |
| 395 | Pd4A | (1) | (2) | (1) | (2) | — | 2 | 2 | Ph | Ph1 | H | H | H | H | H |
| 396 | Pd4A | (1) | (2) | (1) | (2) | — | 2 | 2 | Ph | H | Ph1 | H | H | H | H |
| 397 | Pd4A | (1) | (2) | (1) | (2) | — | 2 | 2 | Ph | Ph1 | Ph1 | H | H | H | H |
| 398 | Pd4A | (1) | (2) | (1) | (2) | — | 2 | 2 | Ph | H | Ph1 | H | H | H | H |
| 399 | Pd4A | (1) | (2) | (2) | (2) | — | 1 | 3 | Ph | Ph1 | Ph1 | H | H | H | H |
| 400 | Pd4A | (2) | (2) | (1) | (2) | — | 1 | 3 | Np14 | Ph1 | H | H | H | H | H |
| 401 | Pi4A | (1) | (1) | (1) | (2) | H | 3 | 1 | — | H | H | H | H | H | H |
| 402 | Pi4A | (1) | (1) | (1) | (2) | H | 3 | 1 | Ph | CH3 | H | H | H | H | H |

TABLE 17-continued

| | | | | | | | | | | | | | | |
|---|---|---|---|---|---|---|---|---|---|---|---|---|---|---|
| 403 | Pi4A | (1) | (2) | (1) | (1) | H | 3 | 1 | — | H | C3H7 | H | H | H | H |
| 404 | Pi4A | (1) | (2) | (1) | (1) | H | 2 | 2 | Ph | CH3 | CH3 | H | H | H | H |
| 405 | Pi4A | (1) | (2) | (1) | (2) | H | 2 | 2 | Ph | Ph1 | H | H | H | H | H |
| 406 | Pi4A | (1) | (2) | (1) | (2) | H | 2 | 2 | Ph | H | Ph1 | H | H | H | H |
| 407 | Pi4A | (1) | (2) | (2) | (1) | H | 2 | 2 | Ph | Ph1 | Ph1 | H | H | H | H |
| 408 | Pi4A | (1) | (2) | (2) | (1) | H | 2 | 2 | Ph | H | Ph1 | H | H | H | H |
| 409 | Pi4A | (1) | (2) | (2) | (2) | H | 1 | 3 | Ph | Ph1 | Ph1 | H | H | H | H |
| 410 | Pi4A | (2) | (2) | (1) | (2) | H | 1 | 3 | FL | Ph1 | H | H | H | H | H |

| No. | $A_2$ | $R_7$ | $R_8$ | $R_9$ | $R_{10}$ | $R_{11}$ | $R_{12}$ | $R_{13}$ | $R_{14}$ | $R_{15}$ |
|---|---|---|---|---|---|---|---|---|---|---|
| 391 | TPh | H | H | H | H | H | H | H | H | H |
| 392 | — | H | H | H | H | H | H | H | H | OCH3 |
| 393 | Ph | H | H | H | H | H | H | H | H | CF3 |
| 394 | Ph | H | H | H | H | H | H | H | H | H |
| 395 | — | H | H | CH3 | H | H | H | H | H | H |
| 396 | — | H | H | H | H | H | H | H | H | F |
| 397 | — | H | H | H | H | H | H | H | H | H |
| 398 | Ph | H | H | H | H | H | H | H | H | H |
| 399 | Ph | H | H | H | H | H | H | H | H | H |
| 400 | — | H | H | H | H | H | H | H | H | H |
| 401 | Qu | H | H | H | H | H | H | H | H | H |
| 402 | — | H | H | C2H5 | H | H | H | H | H | H |
| 403 | Ph | H | H | H | H | H | H | H | H | H |
| 404 | Ph | H | H | H | H | H | H | H | H | H |
| 405 | — | H | H | H | H | H | H | H | H | H |
| 406 | — | H | H | H | H | H | H | H | H | H |
| 407 | — | H | H | H | H | H | H | H | H | H |
| 408 | Ph | H | H | H | H | H | H | H | H | H |
| 409 | Ph | H | H | H | H | H | H | H | H | H |
| 410 | — | H | H | H | H | H | H | H | H | H |

TABLE 18

| No. | X | E | G | J | L | m | n | $A_1$ | $R_1$ | $R_2$ | $R_3$ | $R_4$ | $R_5$ | $R_6$ | $A_2$ | $R_7$ | $R_8$ | $R_9$ | $R_{10}$ | $R_{11}$ | $R_{12}$ | $R_{13}$ | $R_{14}$ | $R_{15}$ |
|---|---|---|---|---|---|---|---|---|---|---|---|---|---|---|---|---|---|---|---|---|---|---|---|---|
| 411 | Pz4A | (1) | (2) | (1) | (2) | 2 | 2 | Ph | CH3 | CH3 | H | H | H | H | Ph | H | H | H | H | H | H | H | H | H |
| 412 | Pz4A | (1) | (2) | (1) | (2) | 2 | 2 | — | Ph1 | H | H | H | H | H | — | H | H | H | H | H | H | H | H | H |
| 413 | Pz4A | (1) | (2) | (1) | (2) | 2 | 2 | Ph | Ph1 | H | H | H | H | H | — | H | H | H | H | H | H | H | H | H |
| 414 | Pz4A | (1) | (2) | (1) | (2) | 2 | 2 | Ph | Ph1 | H | H | H | H | H | Ph | H | H | H | H | H | H | H | H | H |
| 415 | Pz4A | (1) | (2) | (1) | (2) | 2 | 2 | — | H | Ph1 | H | H | H | H | Phen | H | H | H | H | H | H | H | H | H |
| 416 | Pz4A | (1) | (2) | (1) | (2) | 2 | 2 | Ph | H | Ph1 | H | H | H | H | — | H | H | H | H | H | H | H | H | CF3 |
| 417 | Pz4A | (1) | (2) | (1) | (2) | 2 | 2 | — | Ph1 | Ph1 | H | H | H | H | — | H | H | H | H | H | H | H | H | H |
| 418 | Pz4A | (1) | (2) | (1) | (2) | 2 | 2 | Ph | Ph1 | Ph1 | H | H | H | H | — | H | H | H | H | H | H | H | H | H |
| 419 | Pz4A | (1) | (2) | (1) | (2) | 2 | 2 | Ph | Ph1 | Ph1 | H | H | H | H | Ph | H | H | H | H | H | H | H | H | H |
| 420 | Pz4A | (1) | (2) | (1) | (2) | 2 | 2 | Ph | Ph1 | Ph1 | H | H | H | H | — | H | H | H | H | H | H | H | H | H |
| 421 | Pz4A | (1) | (2) | (2) | (1) | 2 | 2 | Ph | CH3 | CH3 | H | H | H | H | Ph | H | H | H | H | H | H | H | H | H |
| 422 | Pz4A | (1) | (2) | (2) | (1) | 2 | 2 | — | Ph1 | H | H | H | H | H | — | H | H | H | H | H | H | H | H | H |
| 423 | Pz4A | (1) | (2) | (2) | (1) | 2 | 2 | Ph | Ph1 | H | H | H | H | H | — | H | H | H | H | H | H | H | H | H |
| 424 | Pz4A | (1) | (2) | (2) | (1) | 2 | 2 | Ph | Ph1 | H | H | H | H | H | Ph | H | H | H | H | H | H | H | H | H |
| 425 | Pz4A | (1) | (2) | (2) | (1) | 2 | 2 | — | H | Ph1 | H | H | H | H | — | H | H | H | H | H | H | H | H | H |
| 426 | Pz4A | (1) | (2) | (2) | (1) | 2 | 2 | Ph | H | Ph1 | H | H | H | H | — | H | H | H | H | H | H | H | H | CF3 |
| 427 | Pz4A | (1) | (2) | (2) | (1) | 2 | 2 | — | Ph1 | Ph1 | H | H | H | H | — | H | H | H | H | H | H | H | H | H |
| 428 | Pz4A | (1) | (2) | (2) | (1) | 2 | 2 | Ph | Ph1 | Ph1 | H | H | H | H | — | H | H | H | H | H | H | H | H | H |
| 429 | Pz4A | (1) | (2) | (2) | (1) | 2 | 2 | Ph | Ph1 | Ph1 | H | H | H | H | Ph | H | H | H | H | H | H | H | H | H |
| 430 | Pz4A | (1) | (2) | (2) | (1) | 2 | 2 | Ph | Ph1 | Ph1 | H | H | H | H | — | H | H | H | H | H | H | H | H | H |
| 431 | Pz4A | (1) | (1) | (2) | (2) | 2 | 2 | Ph | CH3 | CH3 | H | H | H | H | Ph | H | H | H | H | H | H | H | H | H |
| 432 | Pz4A | (1) | (2) | (1) | (2) | 2 | 2 | — | Ph1 | H | H | H | H | H | — | H | H | H | H | H | H | H | H | H |
| 433 | Pz4A | (1) | (2) | (1) | (2) | 2 | 2 | Ph | Ph1 | H | H | H | H | H | — | H | H | H | H | H | H | H | H | Phen9 |
| 434 | Pz4A | (1) | (2) | (1) | (2) | 2 | 2 | Ph | Ph1 | H | H | H | H | H | Ph | H | H | H | H | H | H | H | H | H |
| 435 | Pz4A | (1) | (2) | (1) | (2) | 2 | 2 | — | H | Ph1 | H | H | H | H | — | H | H | H | H | H | H | H | H | H |
| 436 | Pz4A | (1) | (2) | (1) | (2) | 2 | 2 | Ph | H | Ph1 | H | H | H | H | — | H | H | H | H | H | H | H | H | CF3 |
| 437 | Pz4A | (1) | (2) | (1) | (2) | 2 | 2 | — | Ph1 | Ph1 | H | H | H | H | — | H | H | H | H | H | H | H | H | H |
| 438 | Pz4A | (1) | (2) | (1) | (2) | 2 | 2 | Ph | Ph1 | Ph1 | H | H | H | H | — | H | H | H | H | H | H | H | H | H |
| 439 | Pz4A | (1) | (2) | (1) | (2) | 2 | 2 | Ph | Ph1 | Ph1 | H | H | H | H | Ph | H | H | H | H | H | H | H | H | H |
| 440 | Pz4A | (1) | (1) | (2) | (2) | 2 | 2 | Ph | Ph1 | Ph1 | H | H | H | H | — | H | H | H | H | H | H | H | H | H |

TABLE 19

| No. | X | E | G | J | L | M | m | n | $A_1$ | $R_1$ | $R_2$ | $R_3$ | $R_4$ | $R_5$ | $R_6$ |
|---|---|---|---|---|---|---|---|---|---|---|---|---|---|---|---|
| 441 | Pi5A | (1) | (1) | (1) | (2) | (2) | 4 | 1 | — | H | H | H | H | H | H |
| 442 | Pi5A | (1) | (1) | (1) | (2) | (1) | 4 | 1 | Ph | CH3 | Ph1 | H | H | H | H |
| 443 | Pi5A | (1) | (1) | (2) | (1) | (1) | 4 | 1 | — | H | CH3 | H | Ph1 | H | H |

TABLE 19-continued

| | | | | | | | | | | | | | | |
|---|---|---|---|---|---|---|---|---|---|---|---|---|---|---|
| 444 | Pi5A | (1) | (1) | (1) | (2) | (2) | 3 | 2 | Ph | CH3 | CH3 | H | H | H | H |
| 445 | Pi5A | (1) | (1) | (2) | (1) | (2) | 3 | 2 | Ph | Ph1 | H | H | H | H | H |
| 446 | Pi5A | (1) | (2) | (1) | (1) | (2) | 3 | 2 | Ph | H | Ph1 | H | H | H | H |
| 447 | Pi5A | (2) | (1) | (1) | (1) | (2) | 3 | 2 | Ph | Ph1 | Ph1 | H | H | H | H |
| 448 | Pi5A | (1) | (1) | (2) | (2) | (2) | 2 | 3 | Ph | H | Ph1 | H | H | H | H |
| 449 | Pi5A | (1) | (2) | (1) | (2) | (2) | 2 | 3 | Ph | Ph1 | Ph1 | H | H | H | H |
| 450 | Pi5A | (2) | (2) | (1) | (1) | (2) | 2 | 3 | Np14 | Ph1 | H | H | H | H | H |

| No. | A$_2$ | R$_7$ | R$_8$ | R$_9$ | R$_{10}$ | R$_{11}$ | R$_{12}$ | R$_{13}$ | R$_{14}$ | R$_{15}$ |
|---|---|---|---|---|---|---|---|---|---|---|
| 441 | — | H | H | H | H | H | H | H | H | H |
| 442 | — | H | H | H | H | H | H | H | H | OCH3 |
| 443 | Ph | H | H | H | H | H | H | H | H | CF3 |
| 444 | Ph | H | H | H | H | H | H | H | H | H |
| 445 | — | H | H | CH3 | H | H | H | H | H | H |
| 446 | — | H | H | H | H | H | H | H | H | F |
| 447 | — | H | H | H | H | H | H | H | H | H |
| 448 | Ph | H | H | H | H | H | H | H | H | H |
| 449 | Ph | H | H | H | H | H | H | H | H | H |
| 450 | — | H | H | H | H | H | H | H | H | H |

TABLE 20

| No. | X | E | G | J | m | n | A$_1$ | R$_1$ | R$_2$ | R$_3$ | R$_4$ | R$_5$ | R$_6$ | A$_2$ | R$_7$ | R$_8$ | R$_9$ | R$_{10}$ | R$_{11}$ | R$_{12}$ | R$_{13}$ | R$_{14}$ | R$_{15}$ |
|---|---|---|---|---|---|---|---|---|---|---|---|---|---|---|---|---|---|---|---|---|---|---|---|
| 451 | N | (1) | (1) | (2) | 2 | 1 | Ph | H | H | H | H | H | H | Ph | H | H | H | H | H | H | H | H | H |
| 452 | N | (1) | (1) | (2) | 2 | 1 | Ph | CH3 | H | H | H | H | H | Ph | H | H | H | H | H | H | H | H | H |
| 453 | N | (1) | (1) | (2) | 2 | 1 | Ph | H | CH3 | H | H | H | H | Ph | H | H | H | H | H | H | H | H | H |
| 454 | N | (1) | (1) | (2) | 2 | 1 | Ph | CH3 | CH3 | H | H | H | H | Ph | H | H | H | H | H | H | H | H | H |
| 455 | N | (1) | (1) | (2) | 2 | 1 | Ph | Ph1 | H | H | H | H | H | Ph | H | H | H | H | H | H | H | H | H |
| 456 | N | (1) | (1) | (2) | 2 | 1 | Ph | H | Ph1 | H | H | H | H | Np26 | H | H | H | H | H | H | H | H | H |
| 457 | N | (1) | (1) | (2) | 2 | 1 | Ph | Ph1 | Ph1 | H | H | H | H | Ph | H | H | H | H | H | H | H | H | H |
| 458 | N | (1) | (1) | (2) | 2 | 1 | Ph | Ph1 | Ph1 | H | H | H | H | Ph | H | H | CH3 | H | H | H | H | H | H |
| 459 | N | (1) | (1) | (2) | 2 | 1 | Ph | Ph1 | Ph1 | H | H | H | H | Pi | H | H | H | H | H | H | H | H | H |
| 460 | N | (1) | (1) | (2) | 2 | 1 | Np26 | Ph1 | Ph1 | H | H | H | H | Ph | H | H | H | H | H | H | H | H | H |
| 461 | N | (1) | (2) | (2) | 1 | 2 | Ph | H | H | H | H | H | H | Ph | H | H | H | H | H | H | H | H | H |
| 462 | N | (1) | (2) | (2) | 1 | 2 | Ph | CH3 | H | H | H | H | H | Ph | H | H | H | H | H | H | H | H | H |
| 463 | N | (1) | (2) | (2) | 1 | 2 | Ph | H | CH3 | H | H | H | H | Ph | H | H | H | H | H | H | H | H | H |
| 464 | N | (1) | (2) | (2) | 1 | 2 | Ph | CH3 | CH3 | H | H | H | H | Ph | H | H | H | H | H | H | H | H | H |
| 465 | N | (1) | (2) | (2) | 1 | 2 | Ph | Ph1 | H | H | H | H | H | Ph | H | H | H | H | H | H | H | H | H |
| 466 | N | (1) | (2) | (2) | 1 | 2 | Ph | H | Ph1 | H | H | H | H | Ph | H | H | H | H | H | H | H | H | H |
| 467 | N | (1) | (2) | (2) | 1 | 2 | Ph | Ph1 | Ph1 | H | H | H | H | Ph | H | H | H | H | H | H | H | H | H |
| 468 | N | (1) | (2) | (2) | 1 | 2 | Ph | Ph1 | Ph1 | H | H | H | H | Ph | H | H | CH3 | H | H | H | H | H | H |
| 469 | N | (1) | (2) | (2) | 1 | 2 | Ph | Ph1 | Ph1 | H | H | H | H | Pi | H | H | H | H | H | H | H | H | H |
| 470 | N | (1) | (2) | (2) | 1 | 2 | Np26 | Ph1 | Ph1 | H | H | H | H | Ph | H | H | H | H | H | H | H | H | H |

Next, the organic light-emitting device and image display of the present invention will be described.

Figure 1B:
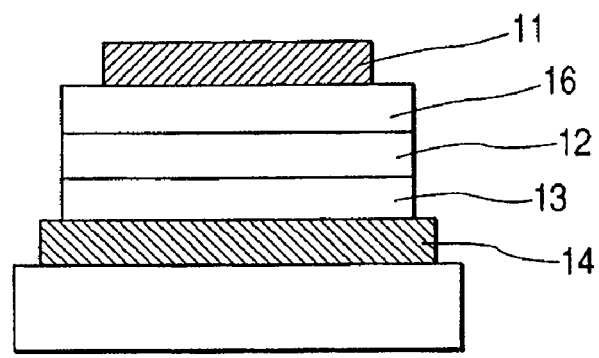
Figure 1C:
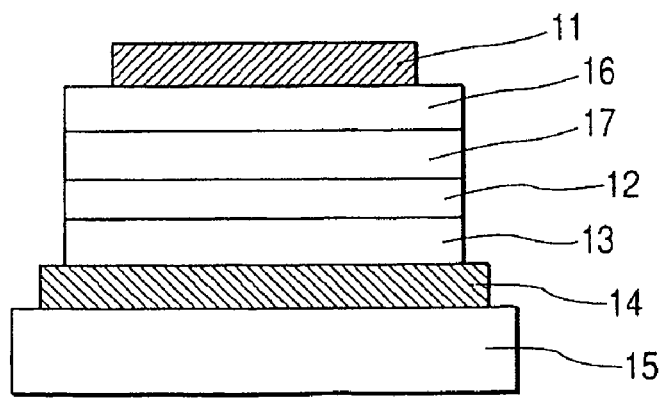

Basic device configurations in accordance with the present invention are shown in FIGS. 1A, 1B and 1C.

In the figures, reference numeral 11 denotes a metal electrode, 12 denotes a light-emitting layer, 13 denotes a hole-transporting layer, 14 denotes a transparent electrode, 15 denotes a transparent substrate, 16 denotes an electron-transporting layer, and 17 denotes an exciton diffusion-prevention layer.

As shown in FIGS. 1A, 1B and 1C, an organic EL device generally comprises a transparent substrate 15, on which formed are a transparent electrode 14 having a film thickness of 50-200 nm, an organic film layer of a multilayer structure and a metal electrode 11 formed to sandwich the organic film layer with the transparent electrode 14.

FIG. 1A shows an example in which the organic layer is consisted of a light-emitting layer 12 and a hole-transporting layer 13. As the transparent electrode 14, ITO or the like having a large work function is used to promote hole injection from the transparent electrode 14 to the hole-transporting layer 13. As the metal electrode 11, aluminum, magnesium or an alloy using those metals having a small work function is used to promote electron injection to the organic layer.

Although it is preferable that the light-emitting layer 12 is formed using an organic compound of the present invention, the hole-transporting layer 13 may be formed by suitably using an electron-donative material, for example, a triphenyldiamine derivative represented by α-NPD shown below.

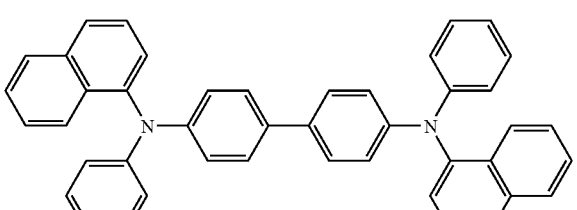

The device configured as mentioned above exhibits a rectifying property, and when an electric field is applied such that the metal electrode 11 is a cathode and the transparent electrode 14 is an anode, electrons are injected into the light-emitting layer 12 from the metal electrode 11, and holes are injected from the transparent electrode 15.

The injected holes and electrons recombine in the light-emitting layer 12 to form excitons thereby emitting light. At this time, the hole-transporting layer 13 plays a role as an electron-blocking layer to increase the recombination efficiency at an interface between the light-emitting layer 12 and the hole-transporting layer 13, which leads to increase in emission efficiency.

Furthermore, in the configuration shown in FIG. 1B, the electron-transporting layer 16 is provided between the metal electrode 11 and the light-emitting layer 12 the configuration of FIG. 1A. By separating the light-emitting function and the electron/hole transporting functions to attain more effective carrier-blocking structure, thereby improving the emission efficiency. As the electron-transporting layer 16, for example, an oxadiazole derivative or the like may be used.

Furthermore, as shown in FIG. 1C, it is also preferable to adopt a four-layer structure in which a hole-transporting layer 13, a light-emitting layer 12, an exciton diffusion-prevention layer 17, an electron-transporting layer 16, and a metal electrode 11 are provided in the mentioned order from the side of a transparent electrode 14 as an anode.

The organic compound of the present invention can be used as a hole-transporting material, electron-transporting material, light-emitting material, host material for dispersing a light-emitting material therein, exciton diffusion-prevention material, charge-injecting material, or the like depending on the selection of the substituent to incorporate. Of these, it can be suitably used as a host material for dispersing, for example, at least one phosphorescent material such as a metal coordination compound, e.g., an iridium coordination compound.

The highly efficient light-emitting device in accordance with the present invention can be applied to those products requiring energy saving and a high luminance. Examples of application include a light source for a display/lighting equipment or a printer, a backlight for a liquid crystal display. When applied to a display, energy saving and provision of a high-visibility, lightweight flat panel display becomes possible. When used as a light source of a printer, a laser light source of laser beam printers now widely used can be replaced by the light-emitting device of the present invention. Independently addressable devices are disposed in an array and a desired exposure is effected to a photoconductive drum to form an image. By using the device of the present invention, the equipment volume can remarkably be reduced. As for a lighting equipment or a backlight, energy-saving effect by the present invention is expectable.

Figure 2:
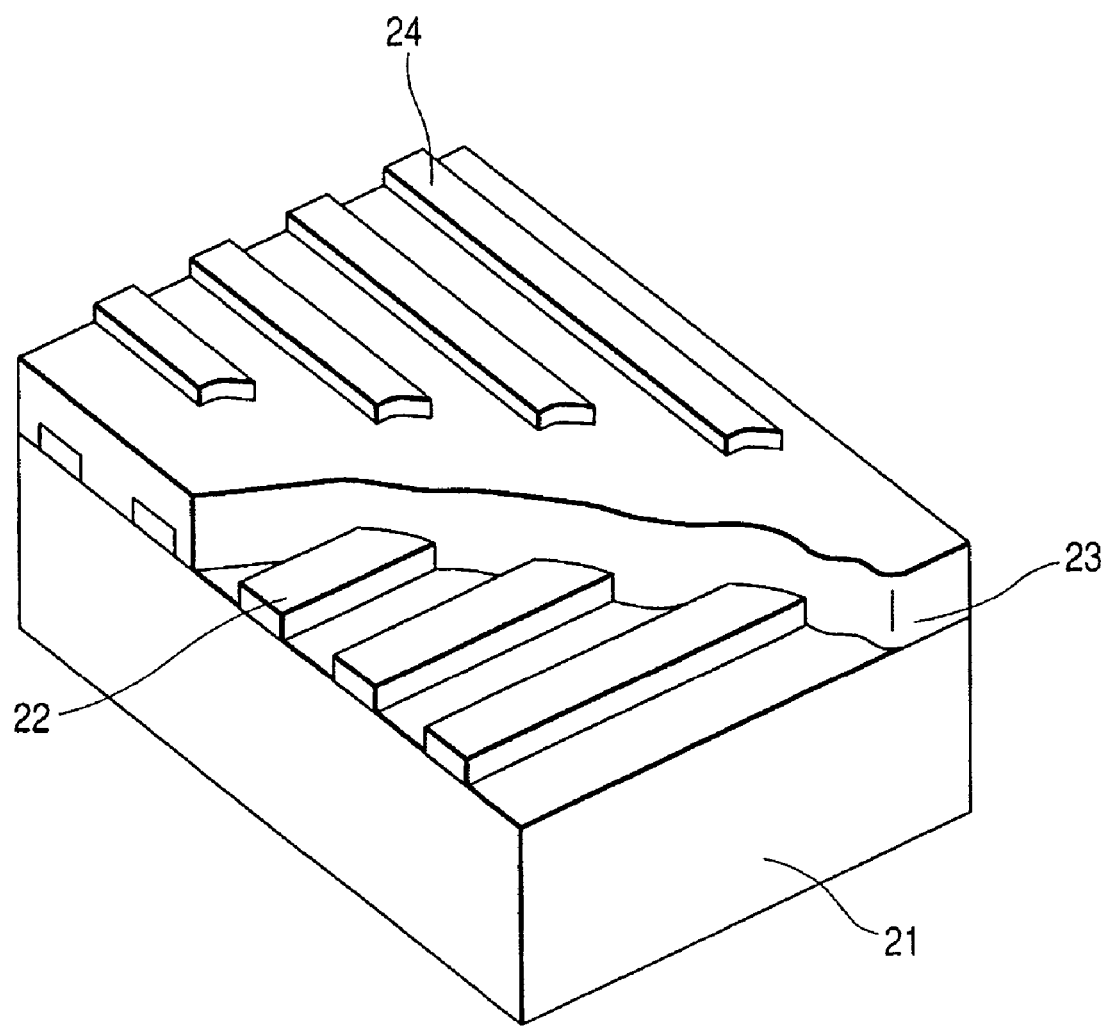
FIG. 2 is a schematic perspective view showing a simple matrix type organic EL device.

Although the device of the present invention can be used as a simple matrix type organic EL device as shown in FIG. 2, it is also envisaged as an application to a display that the system is driven by a TFT driving circuit as an active matrix system.

An example using an active-matrix substrate in a device of the present invention will be described below with reference to FIG. 4.

Figure 3:
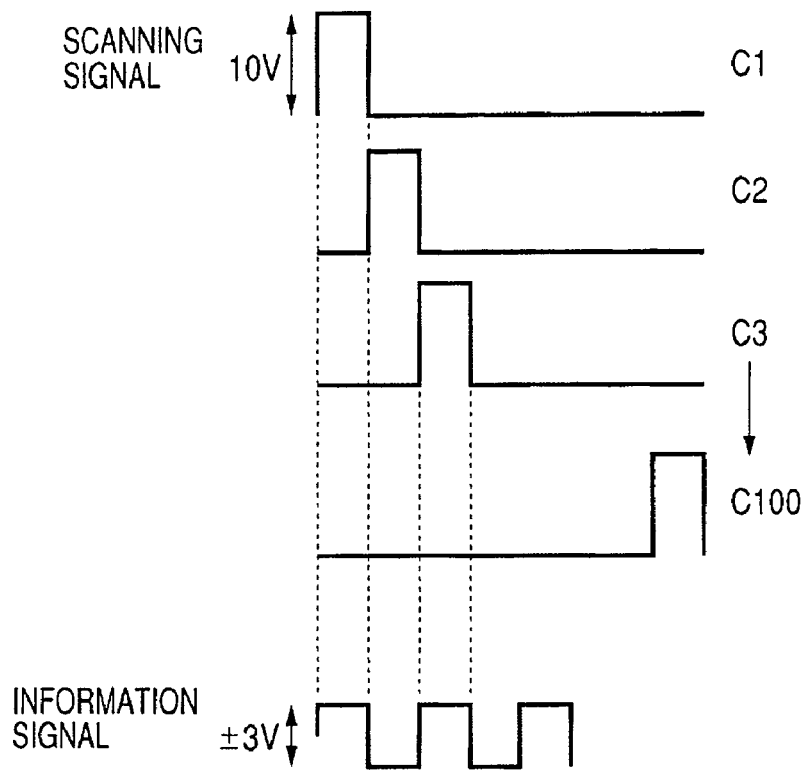
FIG. 3 is a diagram showing a driving signal.
Figure 4:
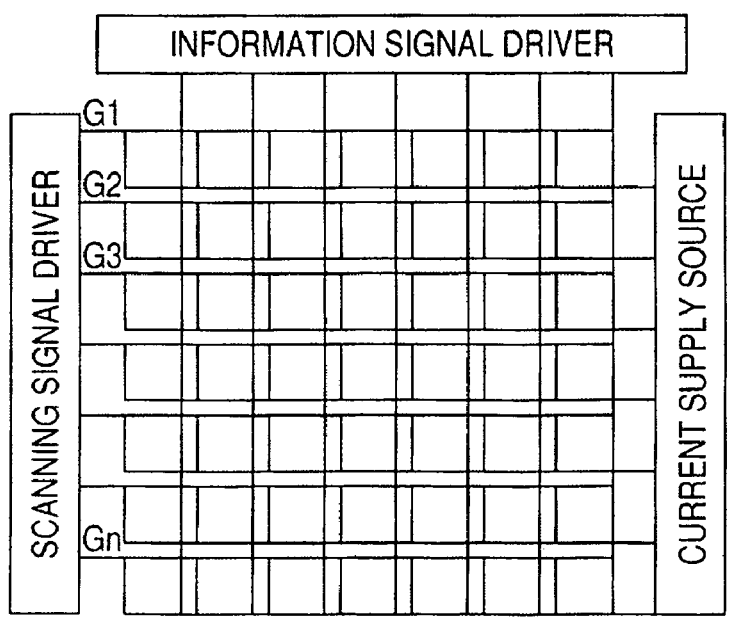
FIG. 4 is a schematic view showing an example of configuration of a panel provided with an EL device and a drive means.

FIG. 4 schematically shows an example of the configuration of a panel equipped with an EL device and a drive means. On a panel, a scanning signal driver, an information signal driver, and a current supply source are disposed and respectively connected to gate selection lines, information signal lines and current supply lines. Display pixel electrodes are disposed at the intersections of the gate selection lines and the information signal lines. The scanning signal driver selects the gate selection lines G1, G2, G3 ... Gn sequentially, and an image signal is applied in synchronization therewith from the information signal driver, thereby displaying an image. An example of the driving signal is shown in FIG. 3.

There is especially no limitation in the switching device of TFT, and either one of a single-crystal silicon substrate, an MIM device, an a-Si type device and the like can readily be adopted.

A multilayer or monolayer organic EL layer/a cathode layer may be stacked sequentially on the above-mentioned ITO electrode to obtain an organic EL display panel. The display panel using the organic compound of the present invention may be driven to attain display that is good in image quality and stable during a long period of use.

EXAMPLES

Example 1

Synthesis of Exemplary Compound No. 34

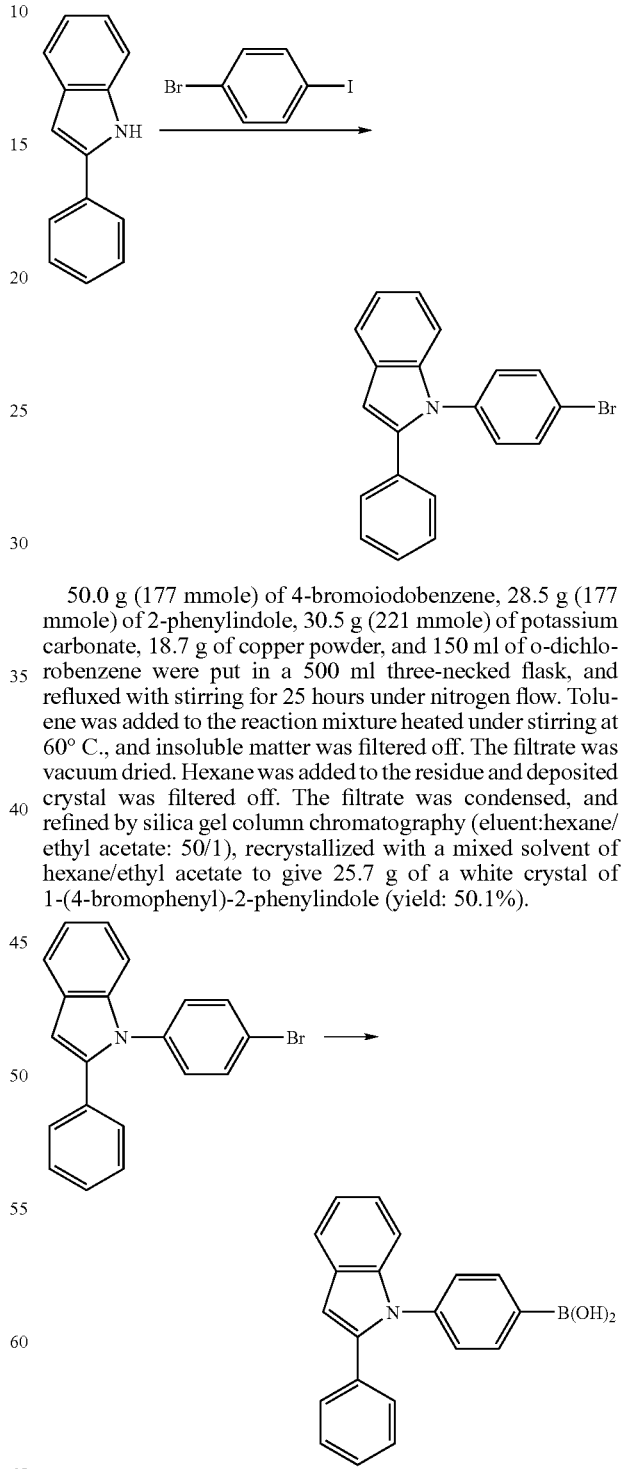

50.0 g (177 mmole) of 4-bromoiodobenzene, 28.5 g (177 mmole) of 2-phenylindole, 30.5 g (221 mmole) of potassium carbonate, 18.7 g of copper powder, and 150 ml of o-dichlorobenzene were put in a 500 ml three-necked flask, and refluxed with stirring for 25 hours under nitrogen flow. Toluene was added to the reaction mixture heated under stirring at 60° C., and insoluble matter was filtered off. The filtrate was vacuum dried. Hexane was added to the residue and deposited crystal was filtered off. The filtrate was condensed, and refined by silica gel column chromatography (eluent:hexane/ethyl acetate: 50/1), recrystallized with a mixed solvent of hexane/ethyl acetate to give 25.7 g of a white crystal of 1-(4-bromophenyl)-2-phenylindole (yield: 50.1%).

18.6 g (53.4 mmole) of 1-(4-bromophenyl)-2-phenylindole and 140 ml of dry tetrahydrofuran were put in a 1000 ml three-necked flask, and 66.7 ml (107 mmole) of 1.6 M-butyl-ithium hexane solution was dropped slowly while keeping the temperature at −63° C. to −62° C. in a dry ice-acetone bath under nitrogen flow. The mixture was stirred at the same temperature for 1 hour after the dropwise addition was ended, and 23.3 g (224 mmole) of trimethyl borate was dropped slowly while keeping the temperature at −63° C. to −60° C. After stirring at the same temperature for another hour, the mixture was gradually heated and left around −3° C. overnight. While keeping the reaction mixture at 12° C. to 13° C. in an ice bath, hydrochloric acid (40 ml of concentrated hydrochloric acid diluted with 20 ml of water) was dropped slowly. This reaction liquid was poured into 1.2 L of ice water, and extracted twice with 250 ml of toluene. The organic layer was washed with water, dried over magnesium sulfate and then vacuumed to dryness. The residue was recrystallized with a mixed solvent of hexane/tetrahydrofuran to give 10.3 g (yield: 61.6%) of a white crystal of 4-(2-phenylindole-1-yl) phenyl boronic acid.

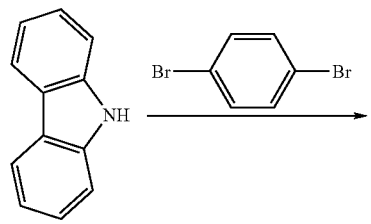

4.30 g (25.7 mmole) of carbazole, 18.19 g (77.1 mmole) of p-dibromobenzene, 0.14 g of palladium acetate and 0.33 g of 1,1'-bisdiphenyl phosphinoferrocene, 3.46 g of (36.0 mmole) sodium t-butoxide and 43 ml o-xylene were put in a 200 ml three-necked flask, and refluxed under stirring for 15 hours and 30 minutes under argon flow. The reaction mixture was filtered using a filter packed with alumina to remove insoluble matter, the filter was washed with toluene and tetrahydrofuran successively. The filtrate and wash liquid were combined and condensed under reduced pressure. Hexane was added to the residue, followed by heating and stirring, then insoluble matter was removed by filtration, and the filtrate was vacuum dried. Hexane was added to the residue and deposited crystal was filtered off. The filtrate was condensed, and refined by silica gel column chromatography (eluent:hexane/toluene:3/1), recrystallized with hexane to give 3.68 g of a white crystal of 9-(4-bromophenyl)carbazole (yield: 44.4%).

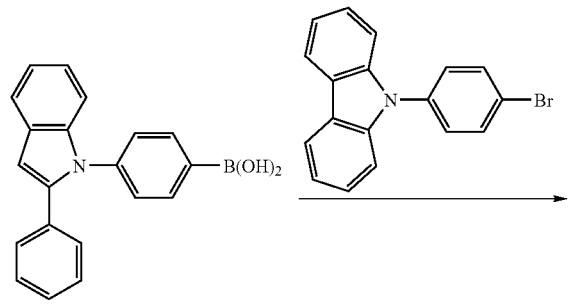

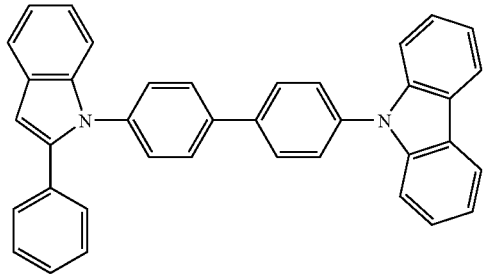

0.78 g (2.49 mmole) of 4-(2-phenylindole-1-yl)phenyl boronic acid and 0.80 g (2.48 mmole) of 9-(4-bromophenyl) carbazole were put in a 20 ml three-necked flask, and 2.5 ml of toluene, 1.5 ml of ethanol, and 2.5 ml of 2M-sodium carbonate solution were put therein, and 0.09 g (0.08 mmole) of tetrakis-(triphenylphosphine) palladium (0) was added under stirring at room temperature under nitrogen flow. Then, the mixture was refluxed with stirring for 5 hours under nitrogen flow. After the reaction was completed, the reaction mixture was cooled to room temperature and deposited crystal was separated by filtration. The crystal was washed with acetone and recrystallized with a mixed solvent of toluene/ethanol. The obtained crystal was refined by alumina column chromatography (eluent:toluene) and crystallize with methanol to give 0.49 g of a white crystal of 4-(2-phenylindole-1-yl)-4'-(carbazole-9-yl)biphenyl (Exemplary Compound No. 34)(yield: 38.6%).

Comparative Example 1

Synthesis of Compound A

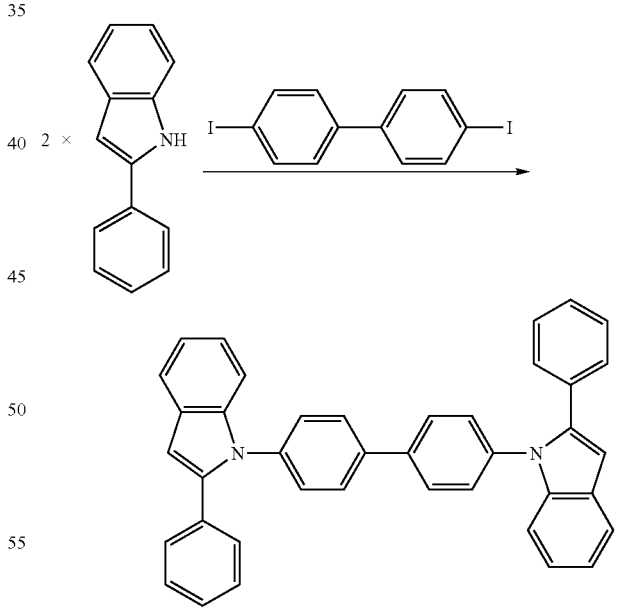

20.1 g (49.5 mmole) of 4,4'-diiodobiphenyl, 25.0 g (128.7 mmole) of 2-phenylindole, 17.8 g (128.7 mmole) of potassium carbonate, 9.4 g of copper powder and 100 ml of o-dichlorobenzene were put in a 300 ml three-necked flask, and refluxed with stirring for 23 hours under nitrogen flow. After the reaction was completed, toluene was added to the reaction mixture heated at 120° C. with stirring, insoluble matter was filtered off. The filtrate was cooled to −15° C. and deposited crystal was filtered. The crystal was dispersed in and washed with acetone, separated by filtration, and recrystallized with N,N'-dimethylformamide added with activated carbon to give 12.7 g of a white crystal of 4,4'-bis(2-phenylindole-1-yl)biphenyl (compound A) (yield: 47.8%).

Example 2

Synthesis of Exemplary Compound No. 46

A white crystal of 4-(2,3-diphenylindole-1-yl)-4'-(carbazole-9-yl)biphenyl (Exemplary Compound No. 46) was obtained following the same procedure as in Example 1 with the exception that 2,3-diphenylindole available from Aldrich Co. was used in place of 2-phenylindole of Example 1.

Comparative Example 2

Synthesis of Compound B

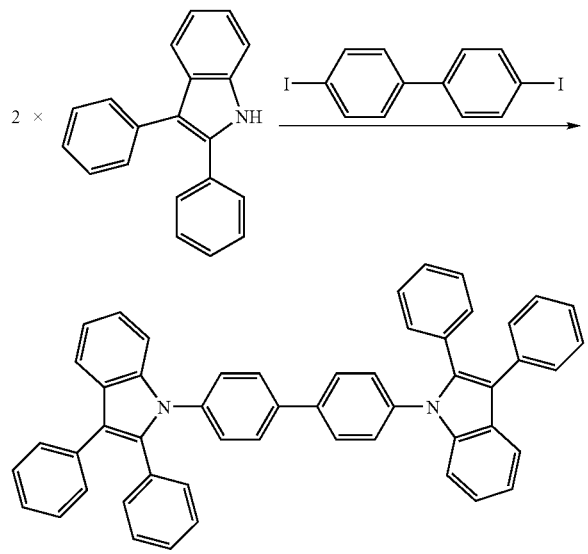

2.90 g (7.14 mmole) of 4,4'-diiodobiphenyl and 5.00 g (18.56 mmole) of 2,3-diphenylindole, 2.70 g (18.56 mmole) of potassium carbonate, 1.4 g of copper powder and 100 ml of o-dichlorobenzene were put in a 300 ml three-necked flask, and refluxed with stirring for 20 hours and 30 minutes under nitrogen flow. After the reaction was completed, the reaction mixture was cooled to room temperature. Toluene and water were added thereto. The mixture was agitated and allowed to separate. The organic layer was washed with water and then vacuum dried, and the residue was recrystallized with tetrahydrofuran added with activated carbon to give 3.10 g of a crystal of 4,4'-bis(2,3-diphenylindole-1-yl)biphenyl (compound B)(yield: 63.0%).

<Measurement>

The melting point, glass transition temperature and crystallization temperatures of the four compounds synthesized in Examples 1 and 2 and Comparative Examples 1 and 2 and 4,4'-bis(carbazole-9-yl)biphenyl (DCBP available from Dojindo Laboratories) were measured by Differential Scanning Calorimetry (DSC) using Pyris1 (trade name) manufactured by Perkin-Elmer, Inc. (Measurement conditions: heating rate of 40° C./min and cooling rate of 40° C./min). The results of these measurements are shown in Table 21. Incidentally, the structural formula of DCBP is shown below.

TABLE 21

DCBP:

| Compound | | Melting point (° C.) | Glass transition temperature (° C.) | Crystallization temperature (° C.) |
|---|---|---|---|---|
| Example 1 | Exemplary Compound No. 34 | 238.0 | 100.8 | Not crystallized to 0° C. |
| Comparative Example 1 | Compound A | 282.5 | Not detectable | 202.5 |
| Example 2 | Exemplary Compound No. 46 | 255.3 | 121.5 | Not crystallized to 0° C. |
| Comparative Example 2 | Compound B | 354.0 | Not detectable | 280.5 |
| — | DCBP | 287.8 | Not detectable | 205.4 |

It can be seen from these results that as compared with the compounds which has only indole rings (compounds A and B) or the compound which has only carbazole rings (DCBP), the compounds of the present invention (Exemplary Compounds 34 and 46) which has both an indole ring and a carbazole ring have a stable glass state, and the present compounds can be expected to form a stable amorphous film by vapor deposition or the like.

Furthermore, the compounds of the present invention (Exemplary Compounds 34 and 46) have a larger solubility to an organic solvent than Compounds A and B and DCBP, and can be easily refined by recrystallization or column chromatography.

Example 3

Figure 5:
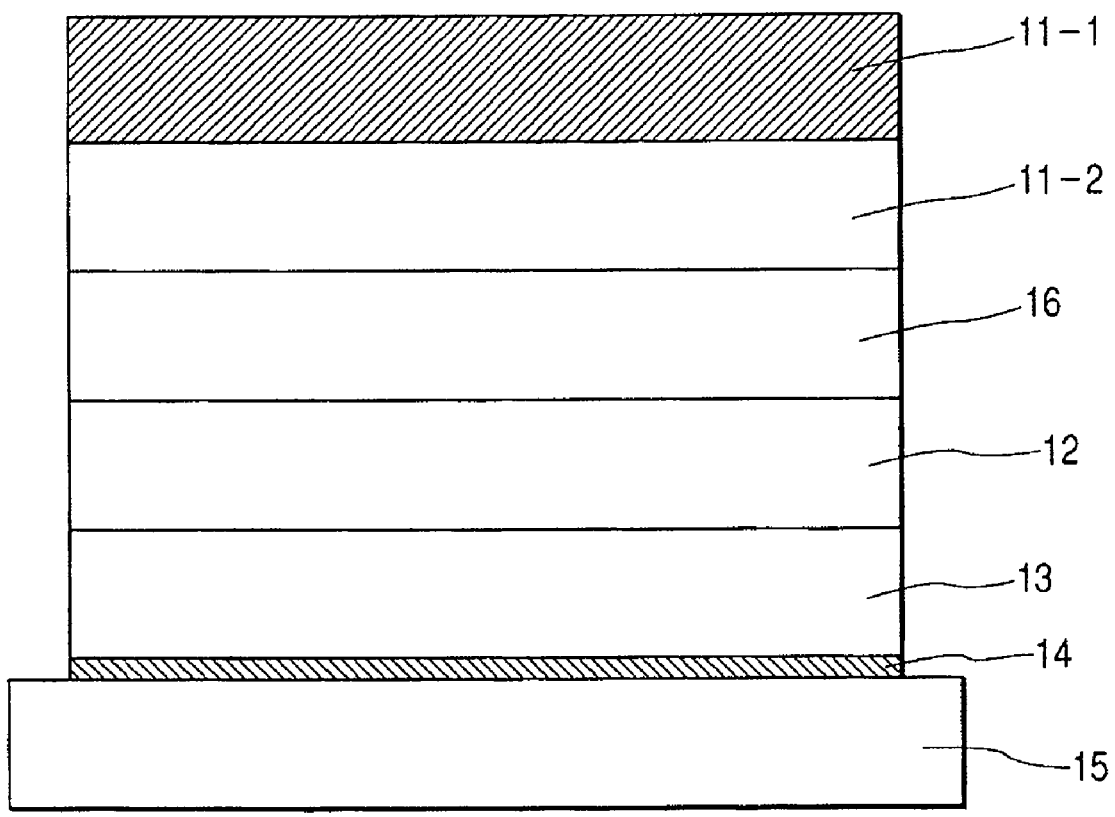
FIG. 5 is a schematic view showing a light-emitting device produced in Example.

As a device structure, a device in which the organic layer was composed of three layers as shown in FIG. 5 was used.

On a glass substrate (transparent substrate 15) was formed an ITO layer (transparent electrode 14) in a thickness of 100 nm by patterning such that the area of the electrode was 3.14 mm$^2$. On the thus formed ITO substrate, the following organic layers and electrode layers were vapor deposited by resistive heating in a vacuum chamber of 10$^{-4}$ Pa to perform continuous film formation.

Hole-transporting layer 13 (40 nm): Compound C; Light-emitting layer 12 (40 nm): Host material+predetermined amount of light-emitting material; Electron-transporting layer 16 (30 nm): Bphen; Metal electrode layer 11-2 (15 nm): KF; and Metal electrode layer 11-1 (100 nm): Al A device was prepared using Exemplary Compound 34 as a host material of the light-emitting layer 12 doped with Ir complex (compound D) as a light-emitting material at a concentration of 10% by weight.

The structural formulae of Compound C, Compound D and Bphen are shown below in the named order, respectively.

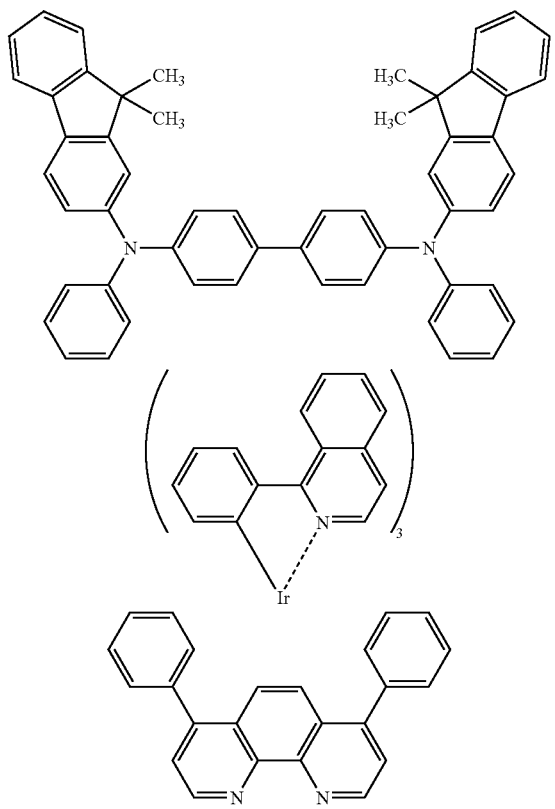

This device achieved a current efficiency of 8.5 cd/A and a power efficiency of 5.9 lm/W at a luminance of 600 cd/m$^2$. The peak of the emission spectrum at this time was 620 nm, and the CIE chromaticity coordinates were (0.68, 0.32).

Comparison of these values with those in the cases where Compound A, DCBP, and TCTA are used as host material is shown in the following table. Incidentally, the structural formula of TCTA is as shown below.

TABLE 22

TCTA:

| Host material | Current efficiency (cd/A) | Power efficiency (lm/W) | Current density under application of 8 v (mA/cm$^2$) | Efficiency saturation current (mA/cm$^2$) | Phosphorescence lifetime (ms) |
|---|---|---|---|---|---|
| DCBP | 5.9 | 1.9 | 2.0 | 0.4 | 532 |
| TCTA | 7.1 | 4.0 | 94.0 | 0.8 | 600 |

TABLE 22-continued

TCTA:

| Host material | Current efficiency (cd/A) | Power efficiency (lm/W) | Current density under application of 8 v (mA/cm$^2$) | Efficiency saturation current (mA/cm$^2$) | Phosphorescence lifetime (ms) |
|---|---|---|---|---|---|
| Compound A | 7.6 | 3.6 | 21.7 | 0.8 | 825 |
| Exemplary Compound No. 34 | 8.5 | 5.9 | 244.7 | 8.0 | 1136 |

As can be seen from the table, the compounds of the present invention having both a carbazole group and an indole group in the molecule structure as a host material have the advantages that more current can be passed therethrough in the case where the same voltage is applied to the device, and therefore the device can be driven at a lower voltage to improve the power efficiency (Advantage 1), and that the efficiency saturation current is large, and therefore a high efficiency can be attained even at a high luminance (Advantage 2).

The term "efficiency saturation current" as employed herein is intended to mean, in terms of the relation between current density and current efficiency, a current density value at a point where the current efficiency begins to decrease with the increase in the current density, as an index of triplet exciton saturation. When a triplet light-emitting material is used as an emission center, because the excitation lifetime thereof is long, a phenomenon is known to occur in which if the amount of current flowing through the device becomes large, the triplet exciton is saturated to lower the emission efficiency. Particularly, improvement in this phenomenon is remarkable. This shows that the decrease in efficiency by the triplet saturation also varies depending on the type of host, and shows that the longer the phosphorescence lifetime of the host, the larger the improvement, wherein the term "phosphorescence lifetime" as employed herein means the time period in which the amount of light after excitation of a triplet emission peak decreases to a half value and is measured and compared at liquid nitrogen temperature (measured by Hitachi fluorescence analyzer F4500. The compounds of the present invention that have both a carbazole group and an indole group in the molecule structure other than those shown in the table each have a long phosphorescence lifetime.

The method of measuring the phosphorescence lifetime of host materials employed herein is as follows. A host material is dissolved in toluene to prepare a solution of 10$^{-6}$ mole/L. This solution is irradiated with an excitation light pulse of 2 ms with a Xe lamp in liquid nitrogen (77K), and the time period in which the amount of light of a peak of fluorescent spectrum decreases to its half value after excitation is measured by a fluorescence spectrophotometer F-4500 available from Hitachi and defined as the phosphorescence lifetime.

For example, Compound B has a phosphorescence lifetime of 580 ms while Exemplary Compound 46 a phosphorescence lifetime of about 880 ms.

Moreover, when a host material is double-doped with Ir complexes (Compound E and Compound F) as phosphorescent materials, an effect is also observed. When such an Iridium complex having a substituent is used as a phosphorescent material, because the material in itself is hard to pass a current therethrough, it is important to use a host that passes an electric current therethrough like Exemplary Compound 34. Incidentally, the structural formulae of Compounds E and F are shown below respectively in the mentioned order.

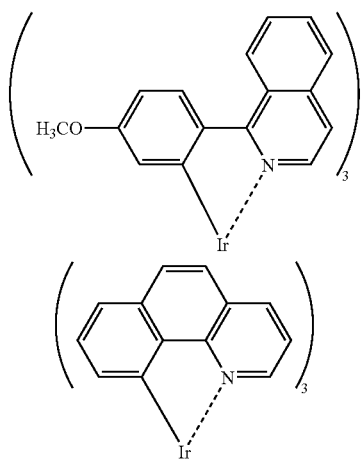

Further characteristic of the compound of the present invention which has a carbazole group and an indole group in the molecular structure is that the highest occupied molecular orbital (HOMO) can be lowered than the compounds having only a carbazole group or an indole group, which leads to an effect of facilitating injection of holes into a dopant and an effect of lowering the lowest unoccupied molecular orbitals (LUMO) to improve electronic injection property. Values of HOMO measured by the Ultraviolet Photoemission Spectroscopy (UPS) are shown in the table below and are 5.65 eV to 5.9 eV for DCBP and TCAT which are compounds having only a carbazole group and are 5.75 eV to 5.93 eV for Compounds A and B which are compounds having only an indole group while the value is deeper as 6.05 eV for Exemplary Compound 34 having both of a carbazole group and an indole group in the molecule structure.

TABLE 23

| Material | DCBP | TCTA | Compound A | Compound B | Exemplary Compound No. 34 |
|---|---|---|---|---|---|
| HOMO (eV) | 5.9 | 5.65 | 5.93 | 5.75 | 6.05 |

As for band gap, as compared with DCBP having a band gap of 3.4 eV, compounds having an indole group tend to have a narrower band gap. For example, it is 2.87 eV for Compound A. This is also considered to be one of the factors of increasing current. Also in this point, the compound differs from the compound disclosed in Macromol. Symp. 125, 1-48 (1997) above.

In order to prevent quenching of the triplet luminescence, the lowest triplet excitation energy level of the host material needs to be higher than the lowest triplet excitation energy level of the phosphorescent material, and as shown in the following table, the lowest triplet excitation energy levels of the compounds (DCBP, TCTA) having only a carbazole group is higher than the lowest triplet excitation energy levels of the compounds (Compound A, Compound B) having only an indole group. By using the compounds (Exemplary Compound 34, Exemplary Compound 46) that have a carbazole group and an indole group in the molecular structure, the lowest triplet excitation energy level can be raised than the compounds having only an indole group.

TABLE 24

| Material | DCBP | TCTA | Compound A | Compound B | Exemplary Compound No. 34 | Exemplary Compound No. 46 |
|---|---|---|---|---|---|---|
| Lowest triplet excitation energy (eV) | 2.61 | 2.84 | 2.48 | 2.44 | 2.49 | 2.45 |

Example 4

Synthesis of Exemplary Compound No. 85

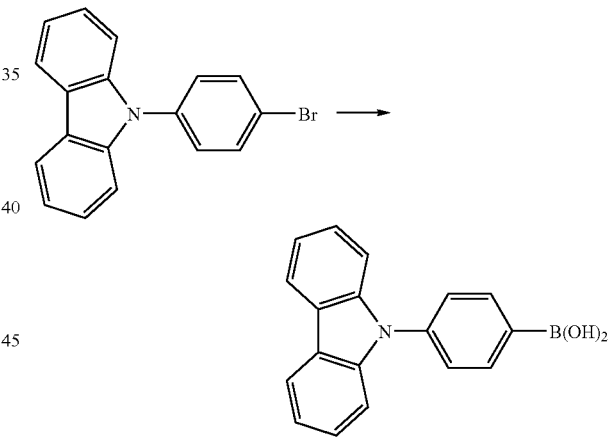

4-(carbazole-9-yl)phenyl boronic acid was synthesized following the same procedure as in Example 1 using 9-(4-bromophenyl)carbazole synthesized in Example 1.

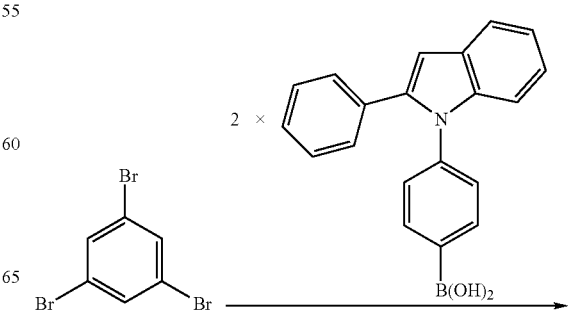

-continued

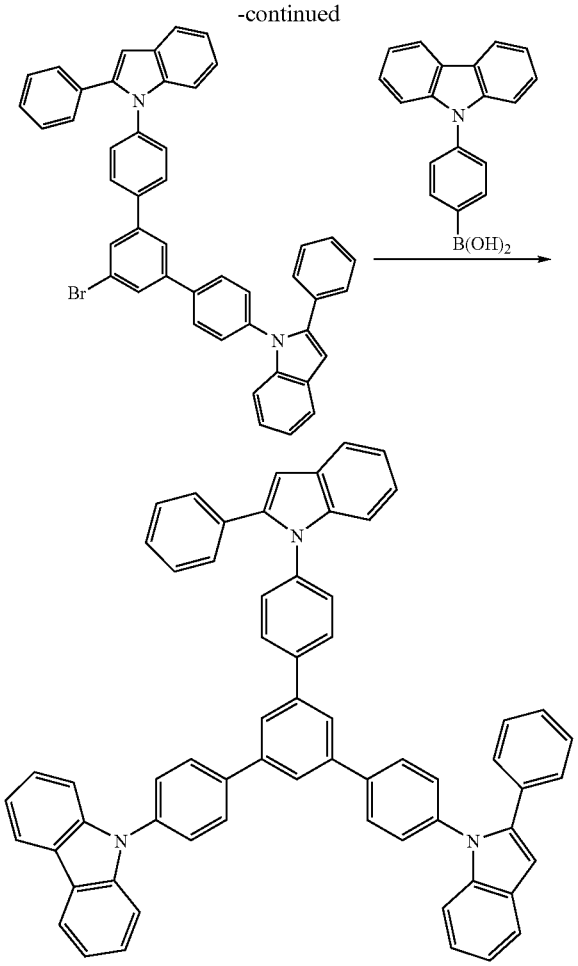

Two equivalent weights of 4-(2-phenylindole-1-yl)phenyl boronic acid was reacted with 1,3,5-tribromobenzene available from Aldrich to synthesize 1-bromo-3,5-bis{4-(2-phenylindole-1-yl)}benzene, and the above-mentioned 4-(carbazole-9-yl)phenyl boronic acid was reacted therewith to give 1-{4-(carbazole-9-yl)phenyl}-3,5-bis{4-(2-phenylindole-1-yl)}benzene. The melting point of this compound was 347° C., and the glass transition temperature was 166° C.

Example 5

Synthesis of Exemplary Compound No. 97

1-{4-(carbazole-9-yl)phenyl}-3,5-bis{4-(2,3-diphenylindole-1-yl)}benzene was obtained following the same procedure as in Example 4 with the exception that 4-(2,3-diphenylindole-1-yl)phenyl boronic acid was used in place of 4-(2-phenylindole-1-yl)phenyl boronic acid of Example 4.

Example 6

Synthesis of Exemplary Compound No. 115

By following the same procedure as in Example 4 with the exception that 4-(carbazole-9-yl)phenyl boronic acid was used in place of 4-(2-phenylindole-1-yl)phenyl boronic acid of Example 4 and 4-(2-phenylindole-1-yl)phenyl boronic acid was used in place of 4-(carbazole-9-yl)phenyl boronic acid, 1-{4-(2-phenylindole-1-yl)phenyl}-3,5-bis-{4-(carbazole-9-yl)phenyl}benzene was obtained. The melting point of this compound was 407° C., and the glass transition temperature was 174° C.

Example 7

Synthesis of Exemplary Compound No. 127

By following the same procedure as in Example 6 with the exception that 4-(2,3-diphenylindole-1-yl)phenyl boronic acid was used in place of 4-(2-phenylindole-1-yl)phenyl boronic acid of Example 6, 1-{4-(2,3-diphenylindole-1-yl)phenyl}-3,5-bis-{4-(carbazole-9-yl)phenyl}benzene was obtained.

Example 8

Synthesis of Exemplary Compound No. 164

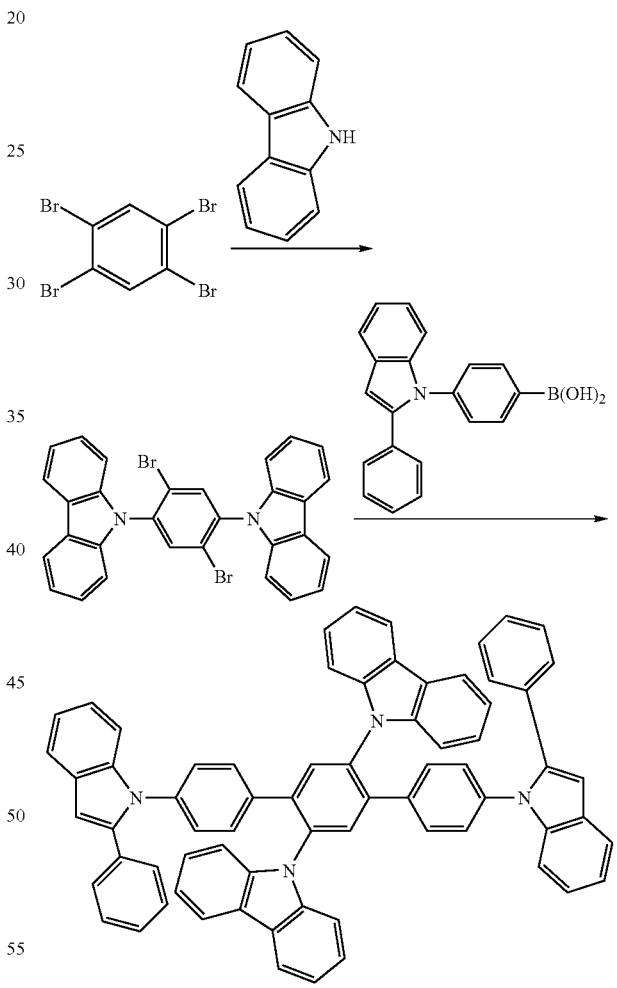

1.16 g (6.1 mmole) of copper iodide and 200 ml of anhydrous dioxane were put in a three-necked flask of 300 ml, 0.41 ml (6.1 mmole) of diaminoethane was dropped at room temperature under nitrogen flow, and the mixture was stirred for 15 minutes at room temperature and heated to 60° C. This solution was allowed to cool to room temperature, 56.8 g (244 mmole) of potassium phosphate, 12.0 g (30.5 mmole) of 1,2,4,5-tetrabromobenzene and 40.8 g (244 mmole) carbazole were added, and heated with stirring at 80° C. under nitrogen flow for 48 hours. After the reaction was completed, the reaction mixture was hot-filtered using Celite to remove insoluble matter. The filtrate was concentrated under reduced pressure. The residue was refined by NH-modified silica gel silica gel column chromatography (eluent:hexane/toluene: 1/2). The obtained crystal was repeatedly recrystallized from toluene and chloroform to give 0.90 g of a white crystal of 1,4-dibromo-3,6-di(carbazole-9-yl)benzene (yield: 5.2%). By reacting two equivalent weight of 4-(2-phenylindole-1-yl) phenyl boronic acid with this 1,4-dibromo-3,6-di(carbazole-9-yl)benzene, 1,4-di(carbazole-9-yl)-2,5-bis{4-(2-phenylindole-1-yl)phenyl}benzene was obtained. The melting point of this compound was 376° C., and the glass transition temperature was 184° C.

Example 9

Synthesis of Exemplary Compound No. 176

By following the same procedure as in Example 9 with the exception that 4-(2,3-diphenylindole-1-yl)phenyl boronic acid was used in place of 4-(2-phenylindole-1-yl)phenyl boronic acid of Example 8, 1,4-di(carbazole-9-yl)-2,5-bis-{4-(2,3-diphenylindole-1-yl)phenyl}benzene was obtained.

Example 10

The phosphorescence lifetimes of Compound D mentioned above and Compound G and Ir(ppy)$_3$ shown below were measured using the following measuring method. An Ir complex was dissolved in a mixed solvent of toluene/ethanol/methanol in a mixing ratio of 5:4:1 by weight to prepare a solution of $10^{-6}$ mole/L. This solution was solidified in liquid nitrogen (77K) and irradiated with an excitation light pulse (wavelength: 337.1 nm) of 5 ns with a nitrogen laser (LN120C; manufactured by Laser Photonics Ltd.), and the time period in which the amount of light of a peak of fluorescent spectrum decreases to its half value after excitation was measured by C4334 Streakscope (manufactured by Hamamatsu Photonics) and defined as the phosphorescence lifetime. Compound D had a phosphorescence lifetime of 1.5 µs at 77K while Compound G and Ir(ppy)$_3$ had phosphorescence lifetimes of 7.8 µs and 4.6 µs at 77K, respectively.

In this example, devices of the structure having 4 organic layers shown in FIG. 1C were made and compared with one another. For each device, an alkali-free glass substrate was used as the transparent substrate 15, and an indium tin oxide (ITO) layer of 100 nm in thickness was formed thereon by sputtering and then patterned to prepare the transparent electrode 14. The above-mentioned α-NPD was vacuum evaporated thereon in a thickness of 40 nm as the hole-transporting layer 13. The organic light-emitting layer 12 was formed thereon in a thickness of 30 nm by using the above-mentioned various compounds as host materials and using the above Compounds D and G and Ir(ppy)$_3$ as a light-emitting material through coevaporation in a ratio of 8% by weight. Further, BCP shown below was vacuum evaporated thereon in a thickness of 10 nm as the exciton diffusion-prevention layer 17. Then, Alq3 shown below was evaporated thereon by resistive heating at a vacuum degree of $10^{-4}$ Pa to give an organic film of 30 nm in thickness as the electron-transporting layer 16. Then, an Al—Li alloy layer is disposed in a thickness of 15 nm as an underlying layer for the metal electrode layer 11. Further, as the metal electrode 11, an aluminium film of 100 nm in thickness was evaporated thereon and patterned in such a shape that the area of the electrode facing the transparent electrode 14 is 3 mm². A current-passing endurance test was performed by applying a 12V DC voltage to the thus made device with the ITO electrode being used as an anode and the Al electrode being used as a cathode, and the time it took for the emission luminance to decrease to its half value was measured.

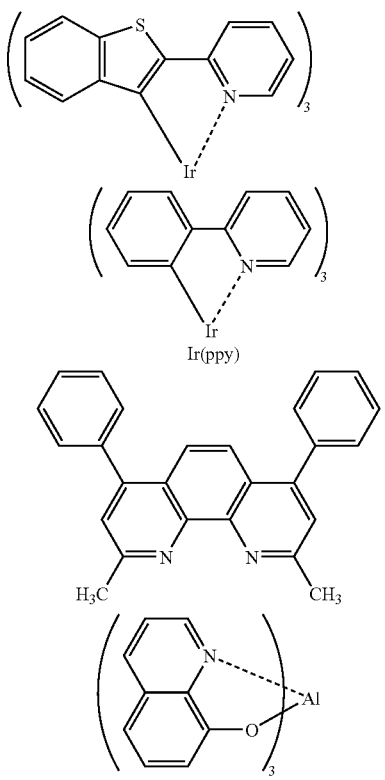

The combination of host material and light-emitting material of the light-emitting layer, the value of (phosphorescence lifetime of host material)/(phosphorescence lifetime of light-emitting material), and the time it takes for the emission luminance to decrease to its half value (simply referred to as "luminance half-value time") for each device are shown in Table 25.

TABLE 25

| Light-emitting Layer | | (phosphorescence lifetime of host material)/ (phosphorescence lifetime of light-emitting material) | Luminance half-value time (hrs) |
|---|---|---|---|
| Host Material | Light-emitting material | | |
| DCBP | Compound G | 6.8 × 10⁴ | 850 |
| DCBP | Ir(ppy)₃ | 1.2 × 10⁵ | 350 |
| DCBP | Compound D | 3.6 × 10⁵ | 1550 |
| Compound B | Compound D | 3.9 × 10⁵ | 1450 |
| Compound A | Compound D | 5.5 × 10⁵ | 1600 |
| Exemplary Compound No. 46 | Compound D | 5.9 × 10⁵ | 4550 |
| Exemplary Compound No. 34 | Compound D | 7.6 × 10⁵ | 4600 |

It has been confirmed from the above results that use of a light-emitting layer in which the fluorescence lifetime at 77K of a host material is 5.8×10⁵ or more times the fluorescence lifetime of a light-emitting material in an organic light-emitting device remarkably improves degradation of luminance of the device and is therefore an effective means to provide a device with high durability.

This application claims priority from Japanese Patent Application Nos. 2003-392090 filed Nov. 21, 2003 and 2004-325838 filed Nov. 10, 2004, which are hereby incorporated by reference herein.

The invention claimed is:

1. An organic compound represented by the following general formula (5):

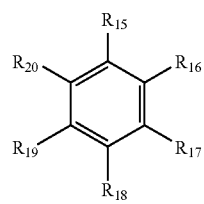

(5)

wherein $R_{15}$, $R_{16}$, $R_{17}$, $R_{18}$, $R_{19}$, and $R_{20}$ is independently selected from a hydrogen atom, a halogen atom, a linear alkyl group having 1-10 carbon atoms (wherein one methylene group or two or more non-adjacent methylene groups of the alkyl group may be replaced by —O—, and a hydrogen atom in the alkyl group may be replaced by a fluorine atom), an unsubstituted or substituted phenyl group, and an unsubstituted or substituted naphthyl group, with the proviso that at least one of $R_{15}$, $R_{16}$, $R_{17}$, $R_{18}$, $R_{19}$, and $R_{20}$ is a partial structure comprising an indole ring represented by the following general formula (1) and at least another of $R_{15}$, $R_{16}$, $R_{17}$, $R_{18}$, $R_{19}$, and $R_{20}$ is a partial structure comprising a carbazole ring represented by the following general formula (2)

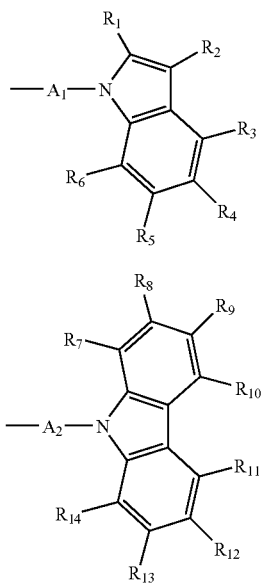

wherein $A_1$ represents an unsubstituted or substituted phenylene group; $A_2$ represents a single bond or an unsubstituted or substituted phenylene group; and $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are independently selected from a hydrogen atom, a halogen atom, a linear alkyl group having 1-10 carbon atoms (wherein one methylene group or two or more non-adjacent methylene groups of the alkyl group may be replaced by —O—, and a hydrogen atom in the alkyl group may be replaced by a fluorine atom), an unsubstituted or substituted phenyl group, and an unsubstituted or substituted naphthyl group.

2. The organic compound according to claim 1, wherein at least three of $R_{15}$, $R_{16}$, $R_{17}$, $R_{18}$, $R_{19}$, and $R_{20}$ are independently a partial structure comprising an indole ring represented by the general formula (1) or a partial structure comprising a carbazole ring represented by the general formula (2).

3. An organic light-emitting device comprising an organic compound layer comprising a plurality of layers, wherein the organic compound layer includes a layer comprising at least one organic compound having a phosphorescence lifetime of 880 ms or more at 77K set forth in claim 1.

4. The organic light-emitting device according to claim 3, wherein the phosphorescence lifetime is 1100 ms or more.

5. The organic light-emitting device according to claim 3, wherein the organic compound is contained in a light-emitting layer.

6. The organic light-emitting device according to claim 5, wherein the light-emitting layer comprises at least one host material and at least one light-emitting material.

7. The organic light-emitting device according to claim 6, wherein the organic compound is a host material.

8. The organic light-emitting device according to claim 6, wherein the fluorescence lifetime at 77K of the host material is $5.8 \times 10^5$ or more times the fluorescence lifetime at 77K of the light-emitting material.

9. The organic light-emitting device according to claim 6, wherein the light-emitting material is a metal coordination compound.

* * * * *